United States Patent
Remes et al.

(10) Patent No.: US 10,006,075 B2
(45) Date of Patent: Jun. 26, 2018

(54) AUTOMATED LOADING MECHANISM FOR MICROBIAL DETECTION APPARATUS

(75) Inventors: Richard Scott Remes, Chesterfield, MO (US); Stanley Michael Philipak, Augusta, MO (US); Mark Joseph Fanning, Florissant, MO (US); Ronnie J. Robinson, St. Charles, MO (US); James Clement Bishop, Columbia, MO (US); Lawrence E. Guerra, Mission, KS (US); Andrew Scherer, Trabuco Canyon, CA (US); Anthony Valentino, Corona, CA (US)

(73) Assignee: bioMerieux, Inc., Durham, NC (US)

( * ) Notice: Subject to any disclaimer, the term of this patent is extended or adjusted under 35 U.S.C. 154(b) by 937 days.

(21) Appl. No.: 12/780,135

(22) Filed: May 14, 2010

(65) Prior Publication Data
US 2011/0124029 A1 May 26, 2011

Related U.S. Application Data

(60) Provisional application No. 61/216,339, filed on May 15, 2009, provisional application No. 61/277,862, (Continued)

(51) Int. Cl.
*G01N 35/00* (2006.01)
*C12Q 1/04* (2006.01)
(Continued)

(52) U.S. Cl.
CPC .............. *C12Q 1/04* (2013.01); *C12M 41/36* (2013.01); *C12Q 1/02* (2013.01); *G01N 35/0099* (2013.01);
(Continued)

(58) Field of Classification Search
CPC ........... G01N 35/02; G01N 2035/0465; G01N 2035/0467; G01N 35/0099; G01N 35/026
(Continued)

(56) References Cited

U.S. PATENT DOCUMENTS

| 3,653,394 A | 1/1972 | Natelson |
| 3,788,450 A | 1/1974 | Tschunt et al. |

(Continued)

FOREIGN PATENT DOCUMENTS

| JP | 2008185597 | 8/2008 |
| WO | 9426874 | 11/1994 |
| WO | 2007006903 | 1/2007 |

OTHER PUBLICATIONS

Co-pending U.S. Appl. No. 12/780,206 "Automated Loading Mechanism For microbial Detection Apparatus" filed May 14, 2010.
(Continued)

*Primary Examiner* — Jonathan M Hurst

(57) ABSTRACT

The present invention is directed to a method and automated loading mechanism for loading an apparatus. The apparatus of the present invention may include a means for automated loading, a means for automated transfer and/or a means for automated unloading of a container (e.g., a specimen container). In one embodiment, the apparatus can be an automated detection apparatus for rapid non-invasive detection of a microbial agent in a test sample. The detection system also including a heated enclosure, a holding means or rack, and/or a detection unit for monitoring and/or interrogating the specimen container to detect whether the container is positive for the presence of a microbial agent. In other embodiment, the automated instrument may include one or more, bar code readers, scanners, cameras, and/or weighing stations to aid in scanning, reading, imaging and weighing of specimen containers within the system.

16 Claims, 27 Drawing Sheets

Related U.S. Application Data filed on Sep. 30, 2009, provisional application No. 61/337,597, filed on Feb. 8, 2010.

(51) Int. Cl.
*C12M 1/34* (2006.01)
*C12Q 1/02* (2006.01)
*G01N 35/04* (2006.01)
*G01N 35/02* (2006.01)

(52) U.S. Cl.
CPC ..... *G01N 35/00603* (2013.01); *G01N 35/026* (2013.01); *G01N 2035/00148* (2013.01); *G01N 2035/0406* (2013.01); *G01N 2035/0453* (2013.01); *G01N 2035/0465* (2013.01)

(58) Field of Classification Search
USPC ........................................................ 435/277
See application file for complete search history.

(56) References Cited

U.S. PATENT DOCUMENTS

| | | | |
|---|---|---|---|
| 3,944,133 A | | 3/1976 | Kessell et al. |
| 4,250,266 A | | 2/1981 | Wade |
| 4,945,060 A | | 7/1990 | Turner et al. |
| 5,110,743 A | | 5/1992 | Windisch et al. |
| 5,164,796 A | | 11/1992 | Di Guiseppi et al. |
| 5,207,986 A | | 5/1993 | Kadota et al. |
| 5,417,922 A | | 5/1995 | Markin et al. |
| 5,498,543 A | | 3/1996 | Berndt |
| 5,516,692 A | | 5/1996 | Berndt |
| 5,518,923 A | | 5/1996 | Berndt et al. |
| 5,573,103 A | * | 11/1996 | Novak et al. .................. 198/604 |
| 5,665,309 A | | 9/1997 | Champxeix et al. |
| 5,715,931 A | * | 2/1998 | Langenbeck .............. 198/860.2 |
| 5,720,377 A | | 2/1998 | Lapeus et al. |
| 5,730,276 A | | 3/1998 | Itoh |
| 5,735,387 A | | 4/1998 | Polaniec et al. |
| 5,817,507 A | | 10/1998 | Berndt |
| 5,817,508 A | | 10/1998 | Berndt |
| 6,060,022 A | | 5/2000 | Pang et al. |
| 6,068,437 A | | 5/2000 | Boje et al. |
| 6,343,690 B1 | | 2/2002 | Britton et al. |
| 6,374,989 B1 | * | 4/2002 | van Dyke, Jr. ......... G01N 35/04 198/367 |
| 6,481,560 B2 | | 11/2002 | Kearney |
| 6,609,872 B2 | | 8/2003 | Itoh |
| 6,669,002 B2 | | 12/2003 | Itoh |
| 6,843,357 B2 | | 1/2005 | Bybee et al. |
| 7,028,831 B2 | | 4/2006 | Veiner |
| 7,063,206 B2 | | 6/2006 | Haan et al. |
| 7,141,213 B1 | | 11/2006 | Pang et al. |
| 7,448,487 B2 | | 11/2008 | Koike |
| 2003/0040104 A1 | * | 2/2003 | Barbera-Guillem ....... 435/286.2 |
| 2003/0223916 A1 | * | 12/2003 | Testrut ..................... B01L 9/06 422/400 |
| 2006/0029519 A1 | | 2/2006 | Nakaya et al. |
| 2006/0216199 A1 | | 9/2006 | Koike |
| 2007/0189926 A1 | | 8/2007 | Le Comte |
| 2007/0269342 A1 | | 11/2007 | Kitagawa |
| 2008/0053790 A1 | | 3/2008 | Itoh |
| 2008/0271546 A1 | * | 11/2008 | Miller et al. ............... 73/863.92 |
| 2008/0318306 A1 | | 12/2008 | Le Comte |
| 2009/0142844 A1 | | 6/2009 | Le Comete |

OTHER PUBLICATIONS

Co-pending U.S. Appl. No. 12/780,322 "Automated Transfer Mechanism for Microbial Detection Apparatus" filed May 14, 2010.
Co-pending U.S. Appl. No. 12/780,234 "Method for Automated Unloading of a Microbial Deteciton Apparatus" filed May 14, 2010.
Co-pending U.S. Appl. No. 12/780,258 "Automated Container Management Device for Micribial Deteciton Apparatus" filed May 14, 2010.
Co-pending U.S. Appl. No. 12/800,467 System for rapid noninvasive detection of a microbial agent in a biological sample and identifying and/or characterizing the microbial agent filed May 15, 2009.
International Search Report and Written Opinion of the International Searching Authority for PCT/US2010/034866 dated Feb. 24, 2011.
Co-pending U.S. Appl. No. 12/780,126 "Automated Microbial Deteciton Apparatus" filed May 14, 2010.
English language abstract of JP2008-185597 from espacenet.com.

* cited by examiner

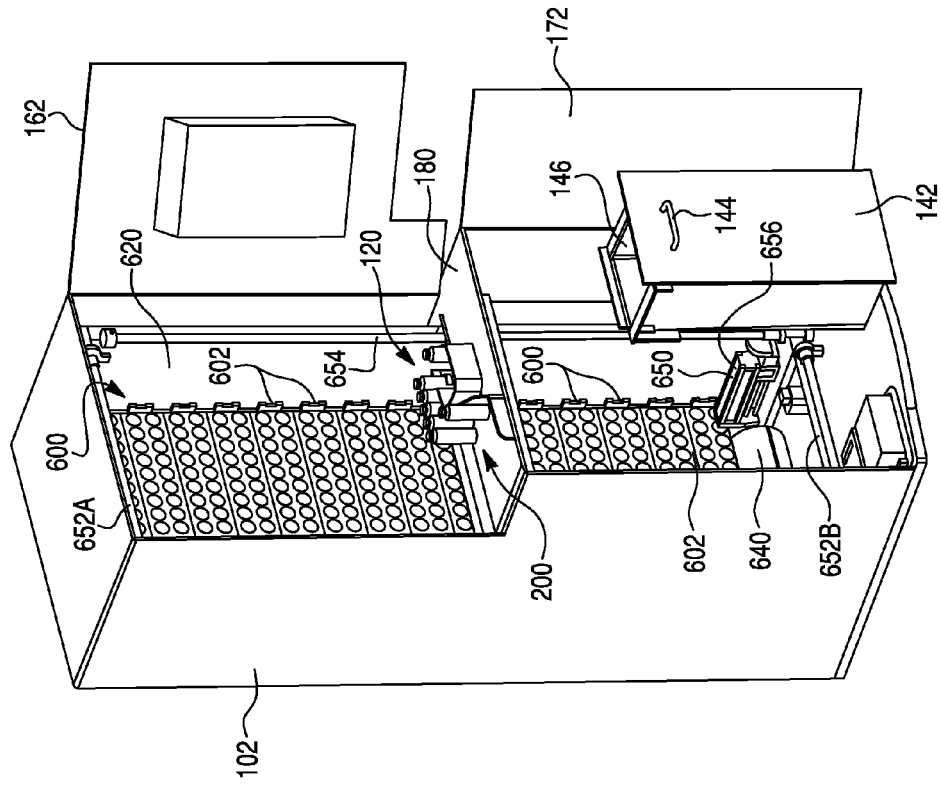
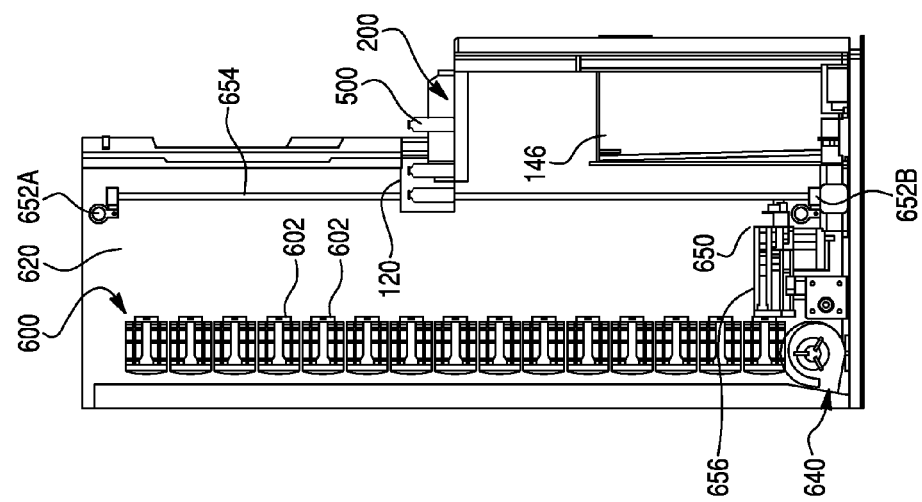

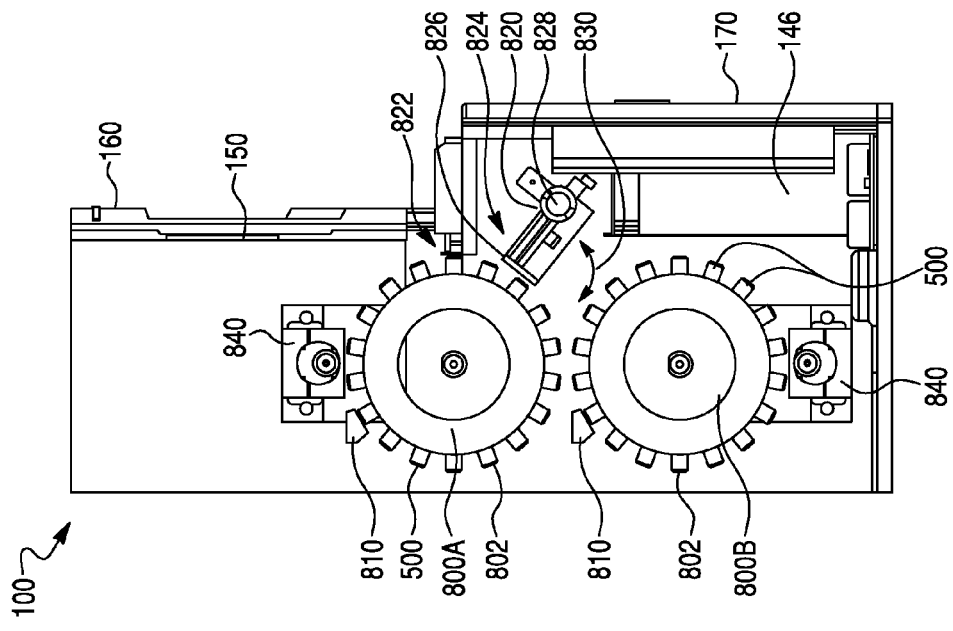
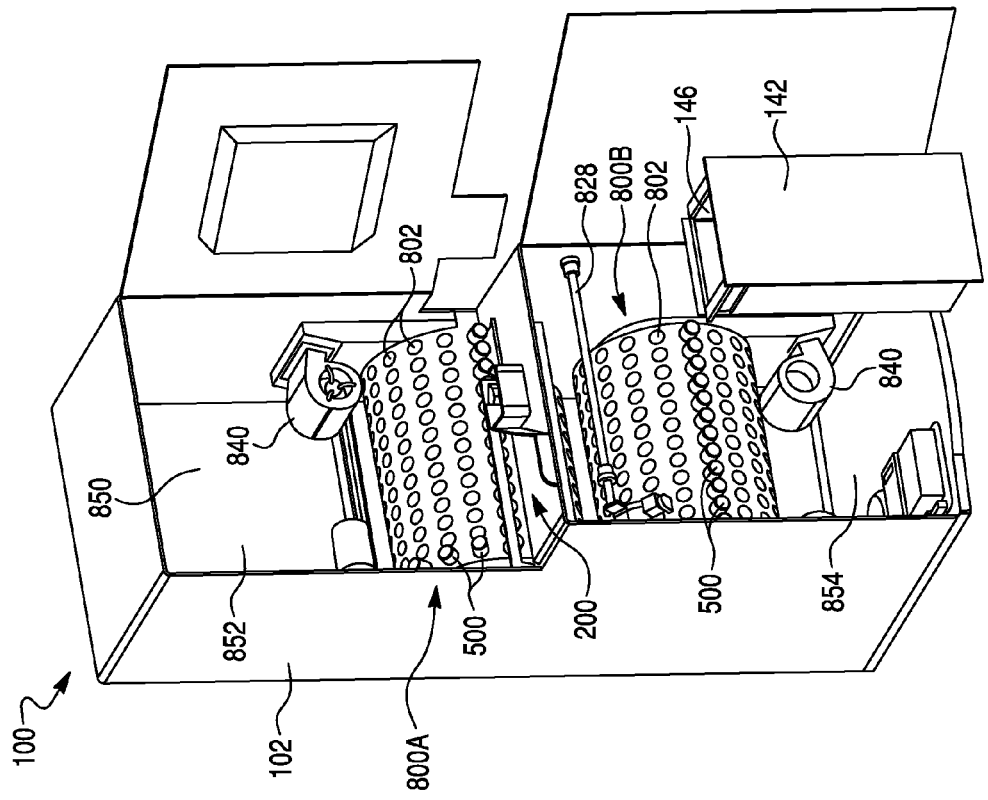

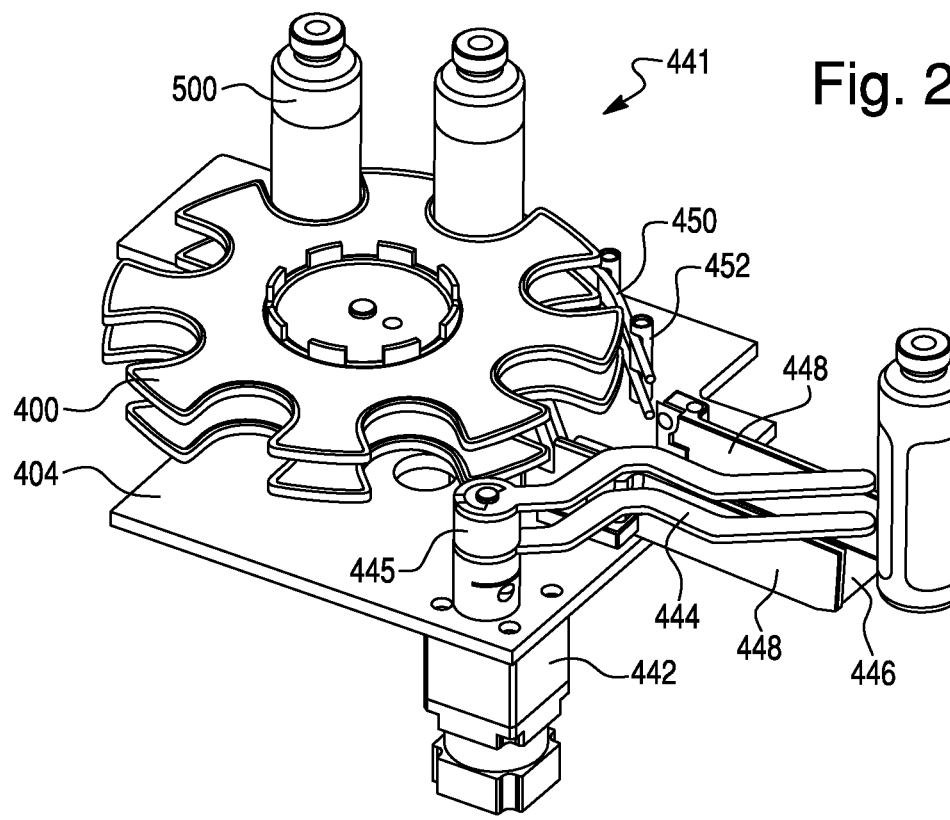

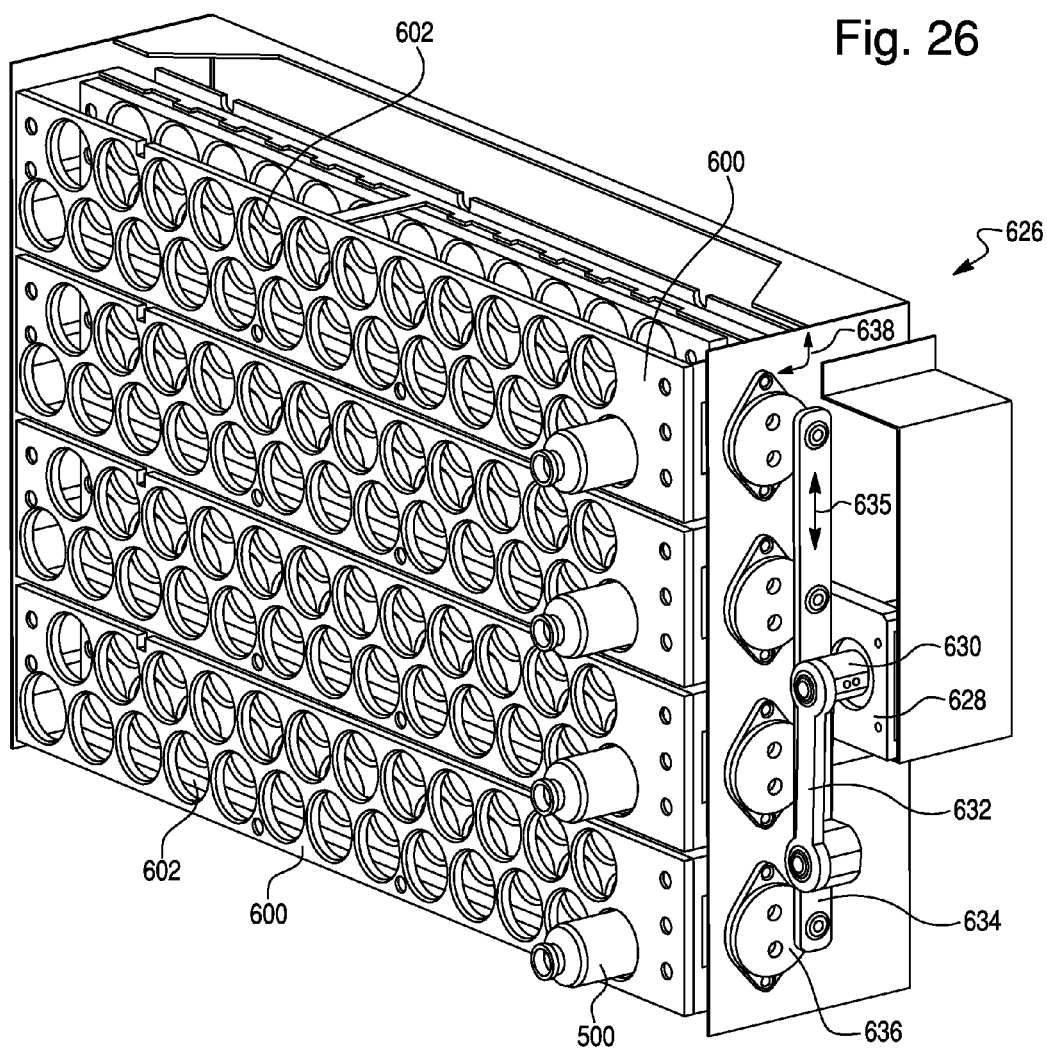

AUTOMATED LOADING MECHANISM FOR MICROBIAL DETECTION APPARATUS

CROSS REFERENCE TO RELATED APPLICATION

This application claims the benefit of: (1) U.S. Provisional Patent Application No. 61/216,339, entitled "System for Combining a Non-invasive Rapid Detection Blood Culture System with an Invasive Microbial Separation and Characterization System", filed May 15, 2009; (2) U.S. Provisional Patent Application No. 61/277,862, entitled "Automated Loading Mechanism for Microbial Detection Apparatus", filed Sep. 30, 2009; and (3) U.S. Provisional Patent Application No. 61/337,597, entitled "Automated Microbial Detection Apparatus", filed Feb. 8, 2010; all of which are incorporated herein.

FIELD OF THE INVENTION

The present invention is directed to an automated system for detecting the presence of a microbial agent or microorganism in a test sample such as a biological sample. Moreover, the automated system builds upon and improves existing detection systems for processing specimen containers, such as culture bottles.

BACKGROUND OF THE INVENTION

The detection of pathogenic microorganisms in biological fluids should be performed in the shortest possible time, in particular in the case of septicemia for which the mortality remains high in spite of the broad range of antibiotics which are available to doctors. The presence of biologically active agents such as a microorganism in a patient's body fluid, especially blood, is generally determined using blood culture bottles. A small quantity of blood is injected through an enclosing rubber septum into a sterile bottle containing a culture medium, and the bottle is then incubated at 37° C. and monitored for microorganism growth.

Instruments currently exist on the market in the U.S. that detect the growth of a microorganism in a biological sample. One such instrument is the BacT/ALERT® 3D instrument of the present assignee bioMérieux, Inc. The instrument receives a blood culture bottle containing a blood sample, e.g., from a human patient. The instrument incubates the bottle and periodically during incubation an optical detection unit in the incubator analyzes a colorimetric sensor incorporated into the bottle to detect whether microbial growth has occurred within the bottle. The optical detection unit, bottles and sensors are described in the patent literature, see U.S. Pat. Nos. 4,945,060; 5,094,955; 5,162,229; 5,164,796; 5,217,876; 5,795,773; and 5,856,175, the entire content of each of which is incorporated by reference herein. Other prior art of interest relating generally to the detection of microorganisms in a biological sample includes the following patents: U.S. Pat. Nos. 5,770,394, 5,518,923; 5,498,543, 5,432,061, 5,371,016, 5,397,709, 5,344,417 and its continuation U.S. Pat. Nos. 5,374,264, 6,709,857; and 7,211,430, the entire content of each of which is incorporated by reference herein.

Substantial, and potentially life saving, clinical benefits for a patient are possible if the time it takes for detection of a microbial agent in a blood sample and reporting the results to a clinician could be reduced. A system that meets this need has heretofore eluded the art. However, such rapid detection of a microbial agent in a biological sample such as a blood sample is made possible by apparatus described herein.

The disclosed system and methods combines a detection system operative to detect a container containing a test sample (e.g., a biological sample) as being positive for microbial agent presence. The systems and methods of this disclosure have the potential to: (a) reduce laboratory labor and user errors; (b) improve sample tracking, traceability and information management; (c) interface to laboratory automation systems; (d) improve work-flow and ergonomics; (e) deliver clinically relevant information; (f) faster results.

Many further advantages and benefits over the prior art will be explained below in the following detailed description.

SUMMARY OF THE INVENTION

An automated system and instrument architecture is described below that provides for automated loading of a detection system for detection of the presence of a microbial agent (e.g., a microorganism) in a sample contained within a specimen container, e.g., a blood culture bottle.

In one embodiment, the present invention is directed to an automated detection apparatus for rapid non-invasive detection of microorganism growth in a test sample, comprising: (a) a sealable specimen container having an internal chamber with a culture medium disposed therein for culturing any microorganisms that may be present in said test sample; (b) a housing enclosing an interior chamber; (c) a detection means located within said interior chamber for the detection of microorganism growth in said specimen container; and (c) a loading means for automated loading of said specimen container into said interior chamber.

In another embodiment, the present invention is directed to an automated detection system for rapid non-invasive detection of microorganism growth in a specimen sample, comprising: (a) a sealable specimen container having an internal chamber containing a culture medium disposed therein for culturing any microorganisms that may be present in said specimen sample; (b) a housing enclosing an interior chamber; (c) an entrance location on said housing for receiving said specimen container into said system; (d) an holding structure contained within said housing and comprising a rack and a plurality of wells for said containers, wherein said holding structure optionally comprises an agitation assembly operable to agitate said specimen container to promote microorganism growth; (e) a detection means within said housing for interrogating said specimen container to detect whether the detection container is positive for the presence of a microbial agent in the biological sample; (f) a loading station located outside of said housing and for receiving a plurality of said specimen containers; (g) a first transport means located outside of said housing for transporting one or more of said specimen containers from said loading station to said entrance location; and (h) a transfer means located within said housing for transferring said specimen container from said entrance location to said holding structure.

In yet another embodiment, the present invention is directed to an automated system for loading a specimen container into an apparatus, comprising: (a) a loading station for loading one or more specimen containers; (b) a conveyor system for transporting said at least one specimen container from said loading station to an entrance location, said conveyor comprising a first conveyor belt operable in a horizontal plane for transporting said one or more containers in a given horizontal direction, a guide rail and a second conveyor belt located in a vertical plane above said first conveyor belt and operable in said vertical plane to provide said specimen container with clockwise or counter-clockwise rotation, thereby preventing two or more of said specimen containers from becoming trapped or jammed at said entrance location; and (c) a transfer means for transferring said one or more specimen containers individually from said entrance location to a holding structure or agitation rack, thereby loading said specimen container into said apparatus.

In still another embodiment, the present invention is directed to an automated loading mechanism for loading a container into an apparatus, comprising: (a) an apparatus comprising a housing enclosing an interior chamber therein; (b) a loading area located outside of said housing for depositing a container; (c) a transport mechanism for transporting said container from said loading area to an entrance location, and subsequently through said entrance location and into said interior chamber; and (d) a robotic transfer arm for transferring said specimen container from said entrance location to a holding means located within said interior incubation chamber of said apparatus, said holding means comprising a plurality of wells for holding one or more of said specimen containers, and wherein said robotic transfer arm is moveable in at least 3-axes and wherein at least one movement is a rotational movement, and thereby loading said specimen container into said apparatus.

In another embodiment, the present invention is directed to A method for the automated loading of a specimen container into a detection system, the method comprising the steps of: (a) providing a specimen container; (b) providing a detection apparatus comprising: a housing enclosing an interior chamber therein, a holding means containing a plurality of wells for holding said specimen containers, and further comprising a detection means for detecting growth of a microbial agent; (c) providing an automated loading means comprising a loading station located on said housing for receiving one or more of said specimen containers, an entrance location in said housing; and a transport means for transporting said one or more of said specimen containers from said loading station to an entrance location, and subsequently through said entrance location and into said interior chamber; (e) depositing one or more specimen containers on said loading station; and (f) transporting said one or more specimen containers from said loading station to said entrance location, and subsequently through said entrance location and into said interior chamber using said transport means, thereby automatically loading said specimen container into said detection apparatus.

BRIEF DESCRIPTION OF THE FIGURES

The various inventive aspects will become more apparent upon reading the following detailed description of the various embodiments along with the appended drawings, in which:

FIG. 5A is a side elevation view of one configuration of the detection system of FIG. 1.

FIG. 5B is a perspective view of the detection system shown in FIG. 5A, with the upper and lower doors open showing the interior chambers and racks for holding multiple containers of the type shown in FIG. 4.

As shown in FIG. 7A, the robotic head is position in a vertical orientation, such that a specimen container held within the robotic head is also in a vertical orientation.

As shown in FIG. 7B, the robotic head is positioned in a horizontal orientation, such that the container held within the robotic head is also in a horizontal orientation.

As shown in FIG. 8A, the gripping mechanism grips the top or cap of the container. FIG. 8B shows the container in an intermediate position in the loading process. FIG. 8B, shows the container after being loaded into the robotic head.

FIGS. 9A and 9B are perspective and side views, respectively, of an alternative configuration of the detection system of FIGS. 1-3 and 5A-5B, with the upper and lower doors open showing an alternative configuration of the container holding structures. In the embodiment of FIGS. 9A and 9B, the racks are arranged in a drum or cylinder-type configuration.

FIG. 16 is a cross-sectional view of the drum-like loading mechanism and vertical chute showing a specimen container falling through the chute. As shown in FIG. 16, the top or cap of the specimen container is held in place briefly by the tapered ledge as the bottom of the container falls through the chute, thereby up-righting the specimen container.

As shown in FIG. 21A, the robotic head is located at a first end of the pivot plated and in a horizontal orientation, such that the specimen container is also orientated in a horizontal orientation. In FIG. 21B, the robotic head is shown located at a second end of the pivot plate and in a vertical orientation, such that the specimen container is also orientated in a vertical orientation.

As shown in FIG. 23, the detection system comprises a first detection apparatus and a second detection instrument.

FIGS. 25A-C show a time-elapsed pusher arm mechanism for pushing a specimen container from a first detection apparatus to a second or down-stream detection apparatus.

FIG. 26 shows a perspective view of the holding structure and agitation assembly shown isolated from the detection system.

FIG. 28A also shows two opposed gripping features or handles and a release mechanism for releasing the plurality of specimen containers at the loading station, as described herein.

As shown in FIG. 29, the detection system includes a release mechanism for releasing one or more specimen containers from the carrier shown in FIGS. 28A-B.

DETAILED DESCRIPTION OF THE INVENTION

Figure 1:
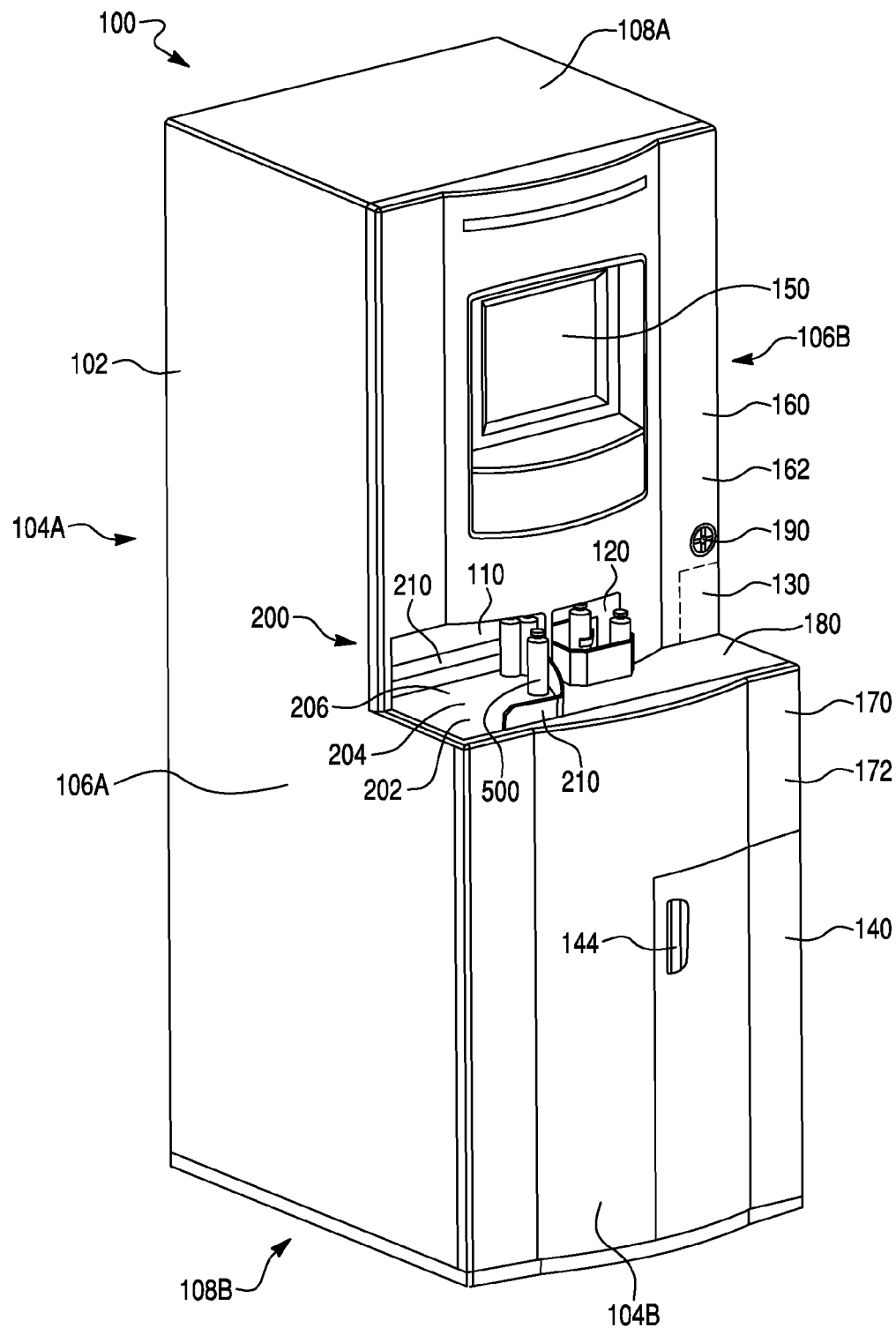
FIG. 1 is a perspective view of an automated system for rapid non-invasive detection of a microbial agent in a test sample. As shown, the system includes an automated loading mechanism.

An automated system or instrument for non-invasive detection of the presence of a microbial agent (e.g., a microorganism) in a test sample contained within a sample container, e.g., a culture bottle, is described herein. One embodiment of the automated system or instrument is described herein in conjunction with FIGS. 1-8C. Other possible embodiments and design alternatives are shown in conjunction with FIGS. 9A-30, and described herein. The automated system can include one or more of the following features: (1) a housing, enclosing an interior chamber; (2) an automated loading mechanism for loading one or more containers into the interior chamber of the system; (3) an automated container management mechanism or locator device for moving or locating a container among various work-flow stations within the system; (4) an automated transfer mechanism, for transfer of a container within the system; (5) one or more container holding structures for holding a plurality of specimen containers, optionally provided with an agitation assembly; (6) a detection unit for detection of microbial growth; and/or (7) a mechanism for automated unloading of a specimen container from the system. In order to better appreciate how the illustrated embodiment of the detection system operate, this specification may describe the automated detection apparatus in the context of a particular detection instrument (a blood culture instrument) and specimen container (a blood culture bottle). However, persons skilled in the art will readily appreciate that the detection apparatus can be practiced in other embodiments, that variations from the specific embodiments disclosed herein can be arrived at to suit particular implementations, and that therefore the present description of a preferred embodiment and best mode for practicing the invention is provided by way of illustration and not limitation.

System Overview

An automated detection system 100 (for example, as illustrated in FIGS. 1-3 and 5A-5B) is described herein that provides a new architecture and method for automated detection of a microbial agent (e.g., a microorganism) that may be present in a test sample or specimen sample. In general, any known test sample (e.g., a biological sample) can be used. For example, the test sample can be a clinical or non-clinical sample suspected of containing one or more microbial agents. Clinical samples, such as a bodily fluid, include, but are not limited to, blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, other body fluids, and the like. Non-clinical samples that may be tested include, but not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, fruit), blood products (e.g., platelets, serum, plasma, white blood cell fractions, etc.), donor organ or tissue samples, biowarfare samples, and the like. In one embodiment, the biological sample tested is a blood sample.

Figure 2:
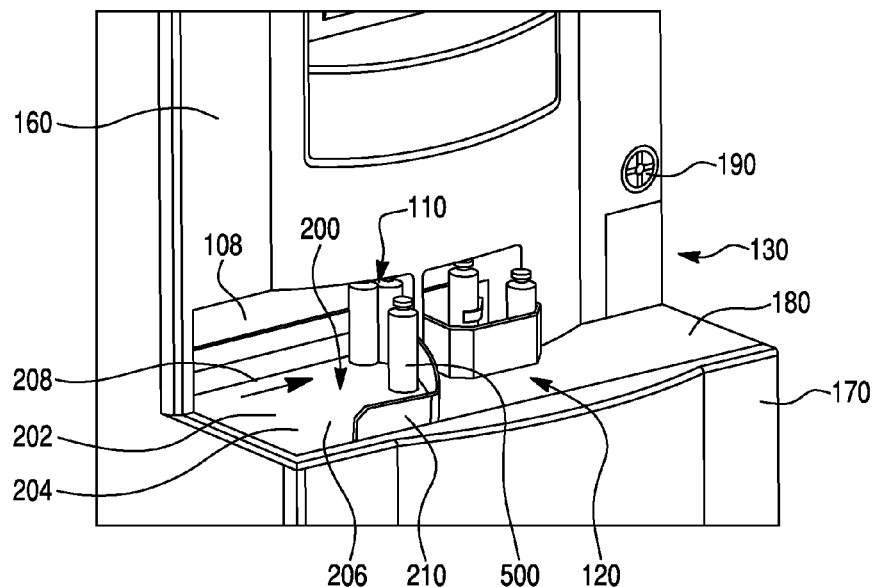
FIG. 2 is a perspective view of the detection system of FIG. 1, showing a close-up view of the automated loading mechanism.
Figure 3:
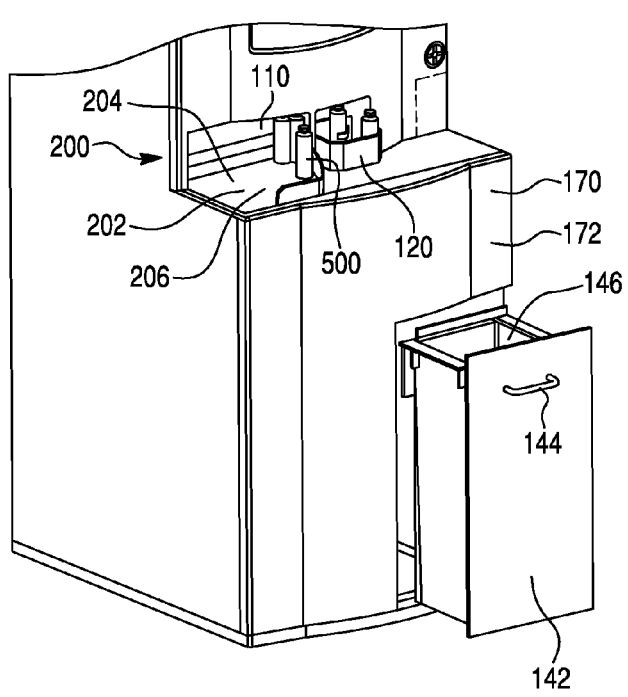
FIG. 3 is a perspective view of the detection system of FIG. 1, which shows an automated loading mechanism and a lower drawer that opens to reveal a waste container for containers that tested negative for presence of a microbial agent.

Referring now to the Figures, several configurations are possible for the detection system 100. As shown, for example, in FIGS. 1-3 and 5A-5B, the automated detection system 100 comprises a housing 102 and one or more automated mechanisms for loading (see, e.g., 200, FIG. 1), moving or locating (not shown), transferring (see, e.g., 650, FIGS. 5A-5B), agitating (not shown) and/or unloading of specimen containers 500 within or from the detection system 100. The housing 102 comprises front and back panels 104A and 104B, opposing side panels (e.g., left-side and right-side panels) 106A and 106B, a top or roof panel 108A and a bottom or floor panel 108B, which form an enclosure, enclosing an interior chamber 620 (see, e.g., FIGS. 5A-5B) of the detection system 100. In one embodiment, the interior chamber 620 of the detection system 100 is a climate-controlled chamber (e.g., a temperature-controlled incubation chamber wherein the temperature is maintained at approximately 37° C.) to promote or enhance microbial growth. As shown in FIGS. 1-3, the housing also may include a first port or container entrance location 110, a second port or misread/error location 120, a third port or positive container exit location 130, a lower access panel 140 (FIG. 1) or drawer 142 (FIG. 3), and/or a user interface display 150. As known in the art, the lower access panel 140 or drawer 142 may include a handle 144. Also as shown in FIG. 1, the housing 102 may also comprise upper and lower sections 160 and 170, optionally each comprising an operable door (i.e., upper and lower doors) 162 and 172 (see, e.g., FIG. 5B). The upper door 162 and lower door 172 are operable to allow access to the interior chamber 620 of the detection system 100. However, as one of skill in the art would appreciate other design configurations are possible. For example, in another possible embodiment, the entire front panel may comprise a single operable door (not shown).

In one design possibility, as shown for example in FIGS. 1-3, the lower section 170 may have a larger profile or footprint than the upper section 160. In accordance with this embodiment the housing of the larger lower section 170 forms a shelf 180 on a top surface of the lower section 170 and adjacent to or in front of the upper section 160. This shelf 180 may provide a user workstation and/or workflow access points to the detection system 100. Furthermore, the shelf 180 may comprise an automated loading means or mechanism 200. The shelf 180 may further provide access locations for the first port or container entrance location 110, the second port or misread/error location 120, and the third port or positive container exit location 130.

In one embodiment, as shown for example in FIGS. 1-3 and 5A-5B, the detection system 100 may comprise an automated loading mechanism 200, for the automated loading of a specimen container 500 into the detection system 100. The automated loading mechanism 200 may comprise a container loading station or area 202, a transport mechanism 204 and a first port or container entrance location 110. In operation, a user or technician can place one or more specimen containers 500 (see, e.g., FIG. 4) at the container loading station or area 202. A transport mechanism 204, for example, a conveyor belt 206, will transport the specimen container to the first port or container entrance location 110, and subsequently through the entrance location 110 and into the detection system 100, thereby loading the container into the system. The automated loading mechanism 200 is described in greater detail herein.

As one of skill in the art would appreciate, other designs may be employed for the automated loading mechanism and are described elsewhere herein. For example, alternative automated loading mechanisms are shown in FIGS. 10-16. In one embodiment, as shown in FIGS. 13-16, and as described in greater detail herein, the detection system 100 may employ a container loading area or reservoir 302 and a drum-like loading device 308 for the automated loading of a specimen container into the detection system 100.

Figure 13:
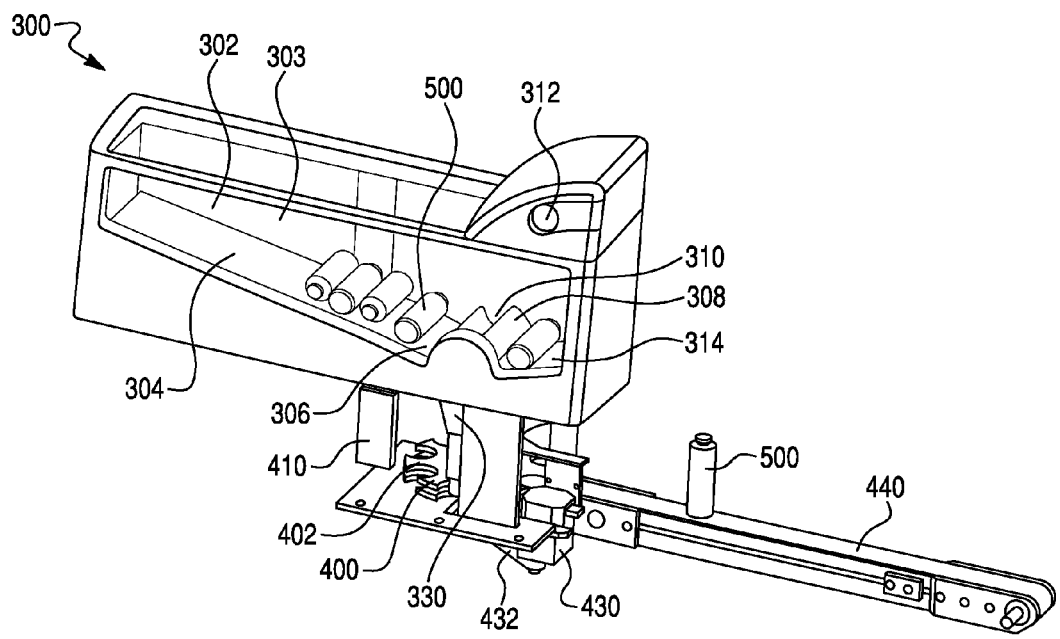
FIG. 13 is a perspective view of one embodiment of an automated loading mechanism shown isolated from the detection system. In accordance with this embodiment, the automated loading mechanism comprises a loading station or area, a transport mechanism and an entrance location, for the fully automated loading of a specimen container. A portion of one side of the loading area has been removed to show additional details of the automated loading mechanism of this embodiment.
Figure 14:
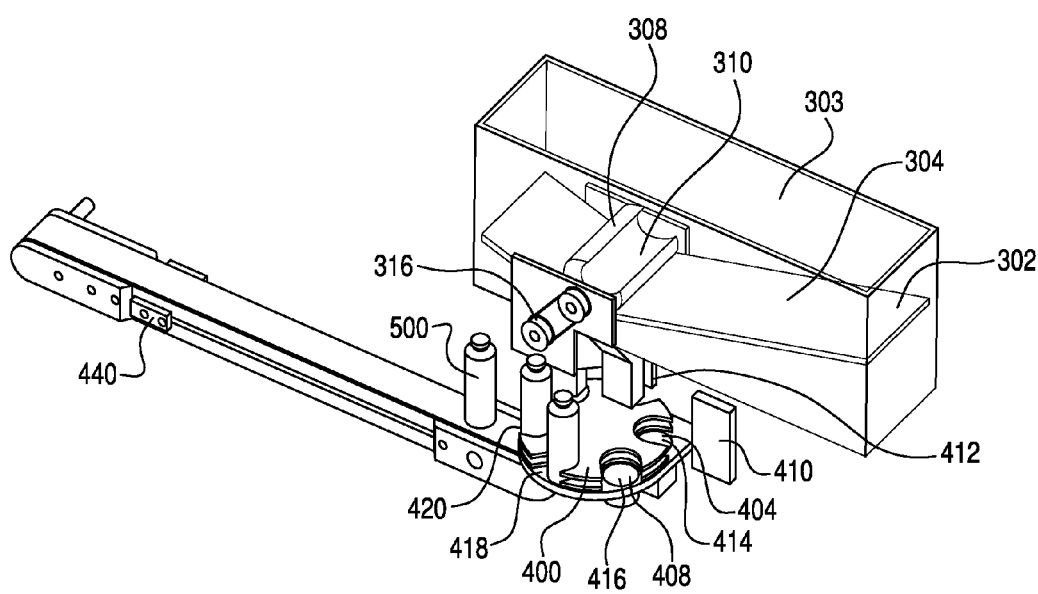
FIG. 14 is another perspective view of the automated loading mechanism shown in FIG. 14. The container loading area is shown as a see through feature to reveal other features of the automated loading mechanism, as described herein.
Figure 15:
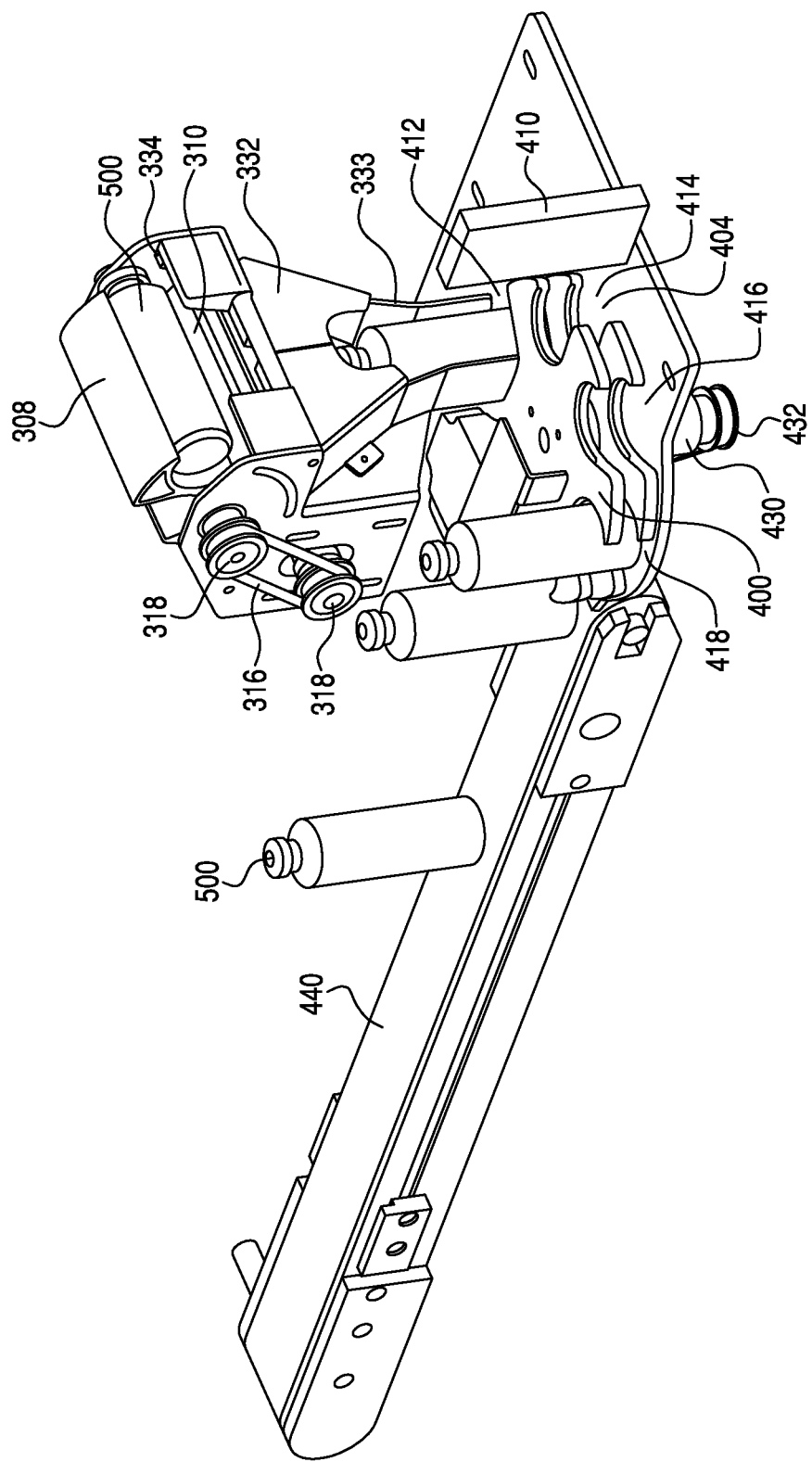
FIG. 15 is a close up perspective view of the drum-like loading mechanism, vertical chute, locating device and system transfer device in FIG. 14. The drum-like loading mechanism, vertical chute, locating device and system transfer device are shown isolated from the detection system.
Figure 18:
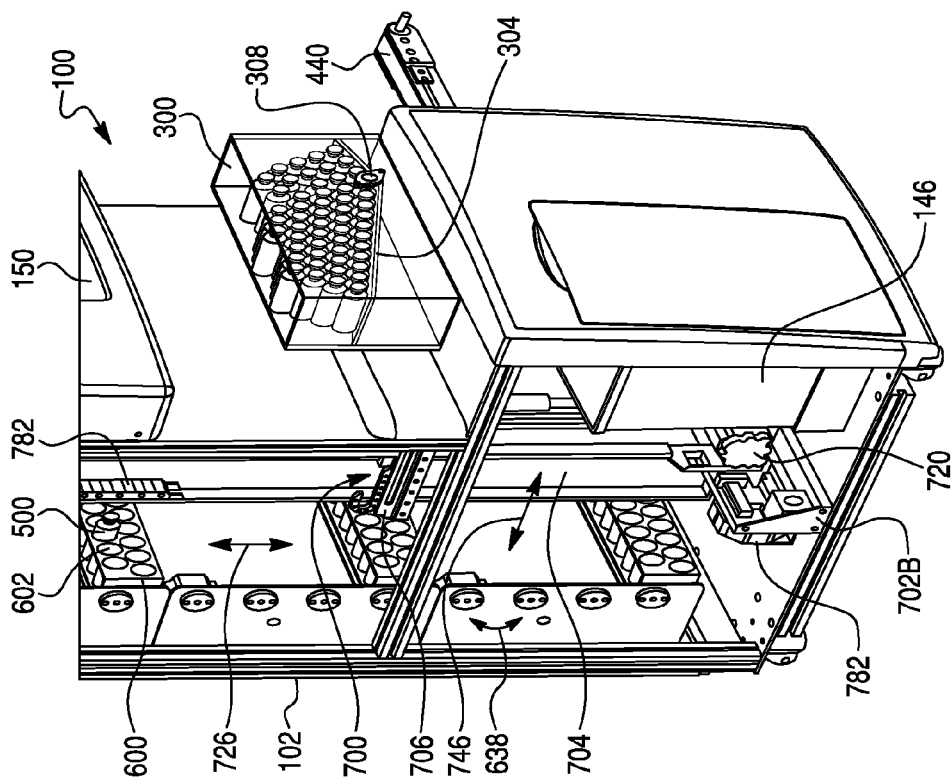
FIG. 18 is a perspective view of the automated detection apparatus comprising an alternative loading mechanism. The container loading area of the automated loading mechanism is shown in a user accessible location on the front of an automated system for rapid non-invasive detection of a microbial agent. The automated detection system and the container loading area are shown with side panels removed and/or as see through features to reveal other features, as described herein.
Figure 19:
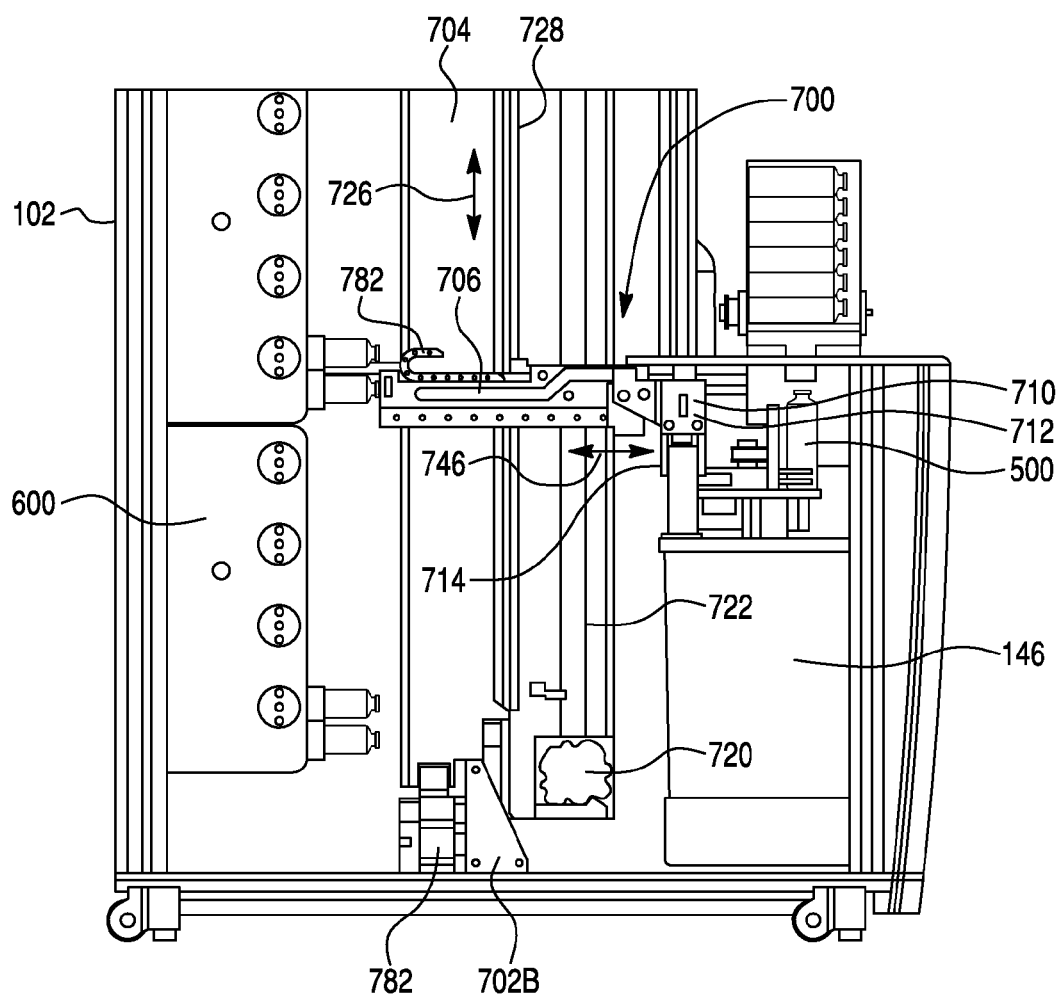
FIG. 19 is a side view of the lower portion of the automated system for rapid non-invasive detection of a microbial agent shown in FIG. 17. The automated detection system is shown with side panel removed to reveal other features of the system, as described herein.

In another embodiment, as shown for example in FIGS. 14-15 and 18, the automated detection system 100 may contain one or more work-flow stations 404 for obtaining one or more measurements, readings, scans and/or images of a specimen container, thereby providing information, such as, container type, container lot number, container expiration date, patient information, sample type, test type, fill level, weight measurement, etc. Furthermore, the one or more work-flow stations 404 may comprise one or more container management stations, such as, a container pick-up station or a container transfer station. For example, the automated detection system may contain one or more of the following work-flow stations: (1) a bar code reading station; (2) a container scanning stations; (3) a container imaging station; (4) a container weighing station; (5) container pick-up station; and/or (6) a container transfer station. In accordance with this embodiment, the detection system 100 may further have a container management means or container locator device 400, as shown, for example, in FIGS. 13-15, 18 and 24. In operation, the container management device or locator device 400, operates to move or otherwise locate a specimen container 500 to one or more work-flow stations 404. In one design configuration, one or more of the work-flow stations are included within the housing 102 of the detection system 100. In one embodiment, as best shown in FIGS. 14-15, the drum or drum-like loading device 308 and vertically orientated chute 332 of automated loading mechanism 300 can operated to deposit or place a specimen container into a locator well 402, as described elsewhere herein. In another embodiment, as best shown, in FIGS. 18 and 24, the transport mechanism 204, or conveyor belt 206, of automated loading mechanism 200 can operate to deposit or place a specimen container into a locator well 402, as described elsewhere herein. As known in the art, the detection system 100 may further comprise one or more guide rails (not shown) to guide the specimen container into the locator well 402. In accordance with both of these embodiments, the container management device or locating device 400 can then rotate to move or locate the specimen container among various work-flow stations 404 within the system, such as for example, a bar code reading station, a container scanning stations, a container imaging station, a container weighing station, container pick-up station, and/or a container transfer station. The container management device or locator device 400 is described in greater detail herein.

As shown, for example, in FIGS. 5A-8C the detection system 100 may also comprise an automated transfer means or mechanism 650 for transferring the specimen containers 500 within the housing 102 of the detection system 100. For example, the transfer mechanism 650 may transfer the specimen container 500 from an entrance location or port 110 (see, e.g., FIGS. 1-3), into the interior chamber 620 of the detection system 100, and place the container 500 into one of the receiving structures or wells 602 contained in one of a plurality of holding structures or racks 600. In another embodiment, the transfer mechanism 650 may also be used to rearrange, transfer or otherwise manage specimen containers 500 within the system. For example, in one embodiment, the transfer mechanism 650 can be used to transfer a specimen container 500, detected as positive for microbial growth (referred to herein as a "positive" container), from the holding structure or rack 600 to a positive container location, such as a positive container exit location or port 130 (see, e.g., FIG. 1) where a user or technician can easily remove the positive container 500 from the detection system 100. In another embodiment, the transfer mechanism 650 can be used to transfer a container 500 determined as negative for microbial growth after a designated time has passed (referred to herein as a "negative" container), from the holding structure or rack 600 to a negative container location within the system (e.g., a negative container waste bin 146 (see, e.g., FIG. 1)) where a user or technician can easily access the waste bin 146 for removal and disposal of the container 500. As one of skill in the art would appreciate, other designs may be employed for the automated transfer mechanism and are described elsewhere herein. For example, another design configuration is described herein in conjunction with FIGS. 17-21B.

The detection system 100 will also include a means for detecting growth (e.g., a detection unit) in the specimen containers 500 (see, e.g., FIG. 27). In general, any known means in the art for detecting microbial growth in a container can be used. For example, as is well known in the art, each holding station or rack 600 may contain a linear scanning optical system that has the capability of non-invasive monitoring of microorganism growth in each specimen container 500. In one embodiment, the optical system can interrogate a sensor (e.g., a Liquid Emulsion Sensor (LES) sensor) 514 (see, e.g., FIG. 4) in the containers 500, thereby detecting for microorganism growth within the container.

The detection system 100 may also include an automated unloading mechanism for the unloading of "positive" and/or "negative" specimen containers 500. This automated unloading mechanism can operate to ensure that once a "positive" or "negative" reading has been made for each specimen container 500, the container 500 is removed from the container receiving structures or wells 602 (see, e.g., FIGS. 5A and 5B), making room for another container to be loaded into the detection system 100, thereby increasing system through-put.

Specimen Container

Figure 4:
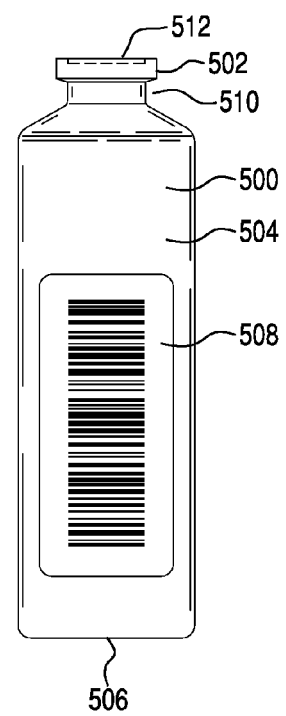
FIG. 4 is a side view of one of the specimen containers processed in the detection system of FIG. 1-3. While the detection container can take a variety of forms, in one embodiment it is configured as a blood culture bottle.
Figure 27B:
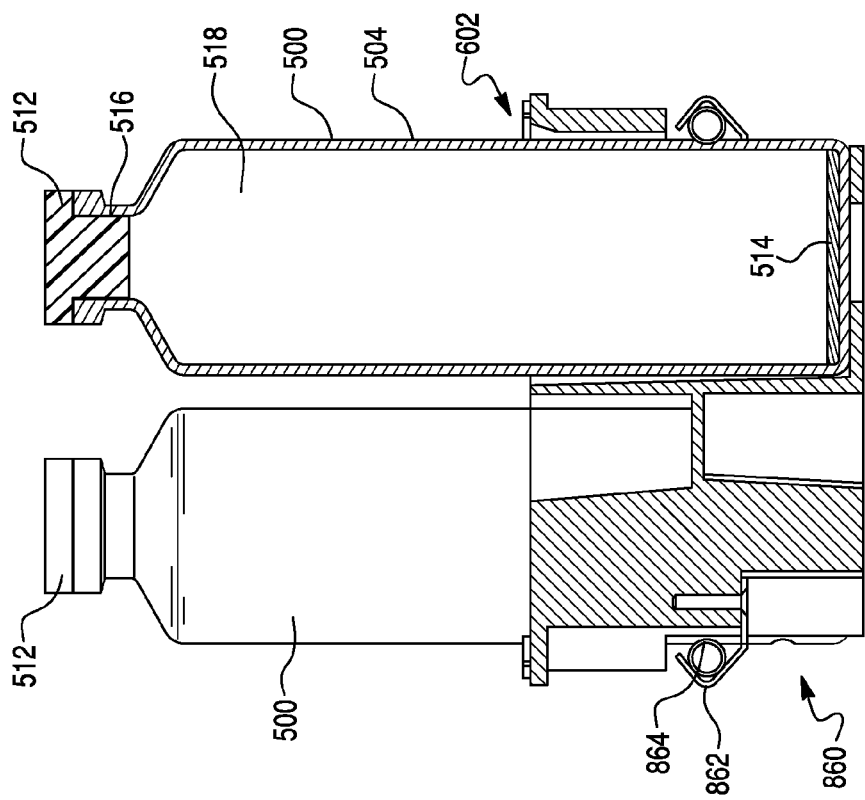
FIG. 27B shows a cross-sectional view of the rack holding structure and retention feature shown in FIG. 27A.

The specimen container 500, shown for example in FIGS. 4 and 27B, and other figures, is shown in the form of a standard culture bottle (e.g., a blood culture bottle). However, the description of a culture bottle (e.g., a blood culture bottle) is offered by way of example and not limitation. As shown in FIG. 4, the specimen container 500 comprises a top portion 502, a body 504, and a base 506. The container 500 may include a bar code label 508 for automated reading of the container 500 within either the detection system or off-line equipment. As shown in FIGS. 4 and 27B, the top portion 502 of the container 500 typically comprises a narrow portion or neck 510 through which an opening 516 extends to provide communication with the interior chamber 518 of the container. As shown in FIG. 27B, the container also includes a closure device 512 (e.g., a stopper), optionally having a pierceable septum and may also have a sensor 514 (e.g., an LES sensor) formed or placed in the bottom of the container 500 for purposes of colorimetric detection of the presence of microbial growth in the container 500. The configuration of the container 500 is not particular important and the inventive system and methods can be adapted to a variety of containers designed for culturing a test sample (e.g., a biological test sample). Containers 500 of the type shown in FIGS. 4 and 27B are well known in the art and described in the patent literature cited in the Background section of this document.

In one embodiment, the specimen containers 500 are inoculated with a test sample (e.g., a clinical or non-clinical biological sample) and are loaded/unloaded into/out of the detection system 100. The container 500 may further comprise a growth or culture medium (not shown) for promoting and/or enhancing microbial or microorganism growth. The use of a growth or culture media (or medium) for the cultivation of microorganisms is well known. A suitable growth or culture medium provides the proper nutritional and environmental conditions for growth of microorganisms and should contain all the nutrients required by the microorganism which is to be cultivated in the specimen container 500. After a sufficient time interval to allow natural amplification of microorganisms (this time interval varies from species to species), the container 500 is tested within the detection system 100 for the presence of microbial or microorganism growth. The testing may occur continuously or on a periodic basis so that the container can be determined as positive for microorganism growth as soon as possible.

In one embodiment, once a container 500 is detected as positive in the detection system 100, the system will notify the operator through an indicator 190 (e.g., a visual prompt), and/or via a notification at the user interface display 150, or by other means.

Automated Loading Means or Mechanism

The detection system 100 may include a means or mechanism for automated loading of a specimen container 500 into the detection system 100. In one embodiment, as shown for example in FIGS. 1-3 and 5A-5B, the automated loading mechanism 200 may comprise a container loading station or area 202, a transport mechanism 204 and an entrance location or port 110. However, as would be appreciated by one of skill in the art, the automated loading mechanism can take on many different configurations. For example, another design configuration of an automated loading mechanism 300 is described herein in conjunction with FIGS. 13-16. The various design configurations described herein are by way of illustration and not limitation. The automated loading mechanisms shown herein (e.g., FIGS. 1-3, 5A-5B and 13-16) are shown schematically and the parts are not to scale.

A user or technician can transport one or more specimen containers 500 to the detection system 100 by any known means and place the containers 500 at a container loading station or area 202. For example, in one embodiment, a user or technician can use a carrier designed to transport a plurality of specimen containers to the loading station or area 202 of the detection system 100.

Figure 28A:
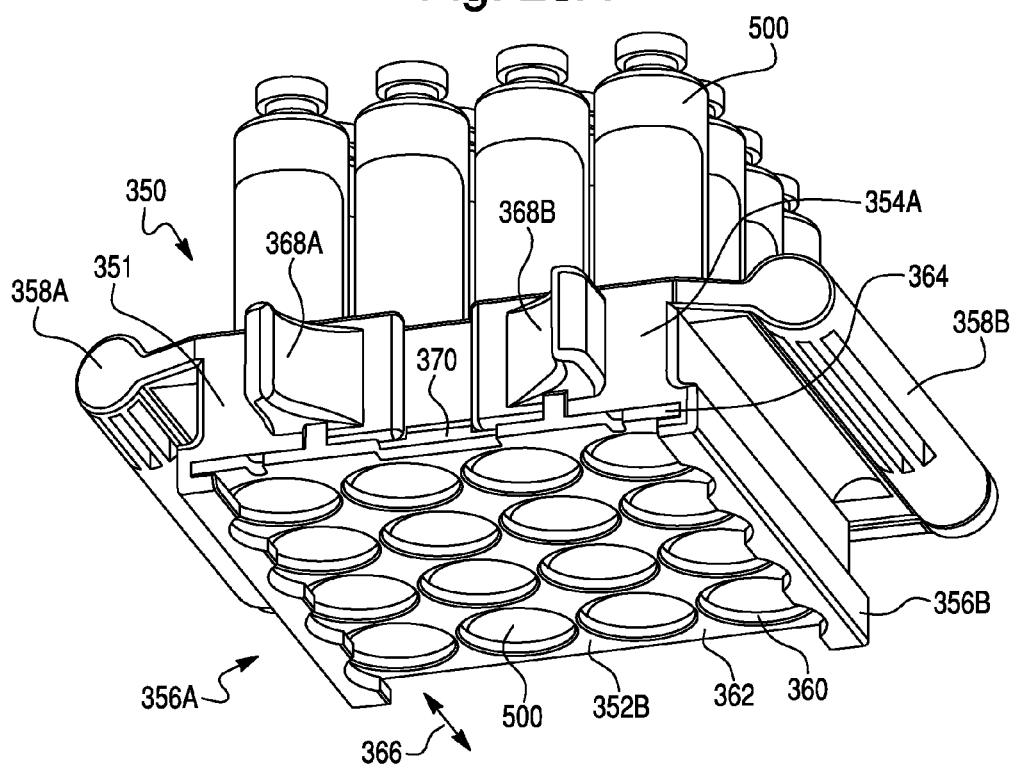
FIG. 28A-B show first and second perspective views of a carrier for carrying a plurality of specimen containers to the detection apparatus. As shown, the carrier comprises a plurality of holding wells for holding a plurality of specimen containers.
Figure 28B:
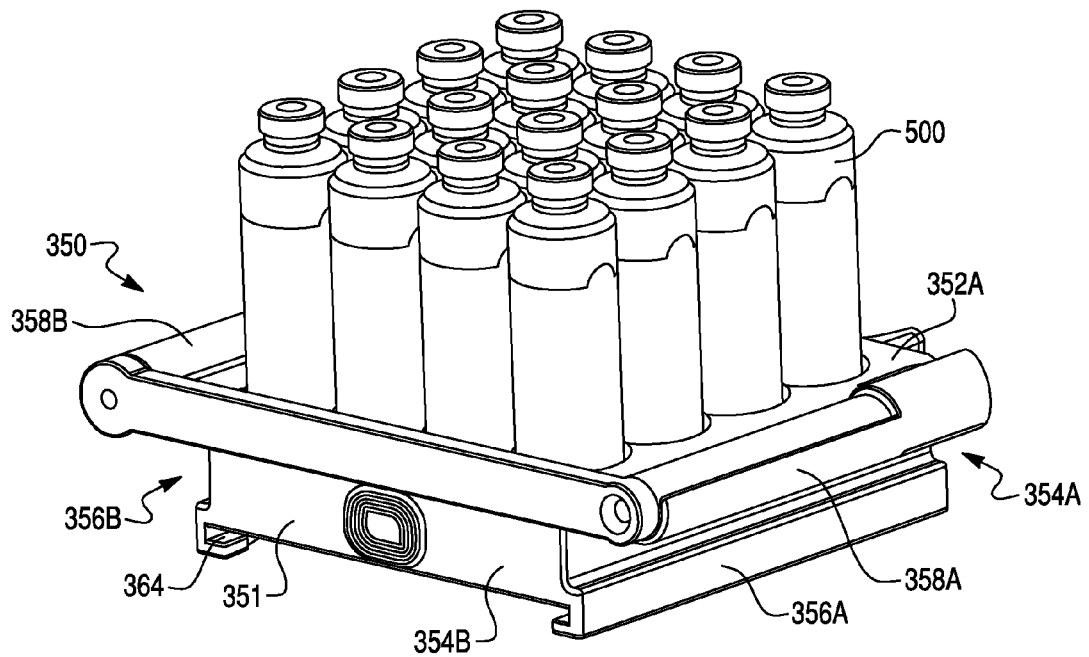

One possible carrier design is shown in FIGS. 28A and 28B. As shown in FIGS. 28A and 28B, the carrier 350 comprises a body 351 having top and bottom surfaces 352A and 352B, respectively, front and back surfaces 354A and 354B, respectively, opposing side surfaces 356A and 356B (e.g., a right side surface and left side surface), respectively, and a pair of opposing user handles 358A and 358B, attached to said opposing side surfaces 356A, 356B. The body further comprises a plurality of through holes 360, each configured to hold a single specimen container 500 therein. The body 351 may also comprise a slide plate 362 operable within a slide joint 364 to slide back-and-forth (see, e.g., arrow 366 in FIG. 28A) between a "closed" position, to retain the specimen containers 500 loaded within the carrier 350, and an "open" position, to release the specimen containers 500 from the carrier 350, and deposit them onto or into an automated loading mechanism. The slide joint 364 may further comprise a spring, or like means, for locking the slide plate 362 in the "closed" position during transport by a user to a detection system.

Figure 29:
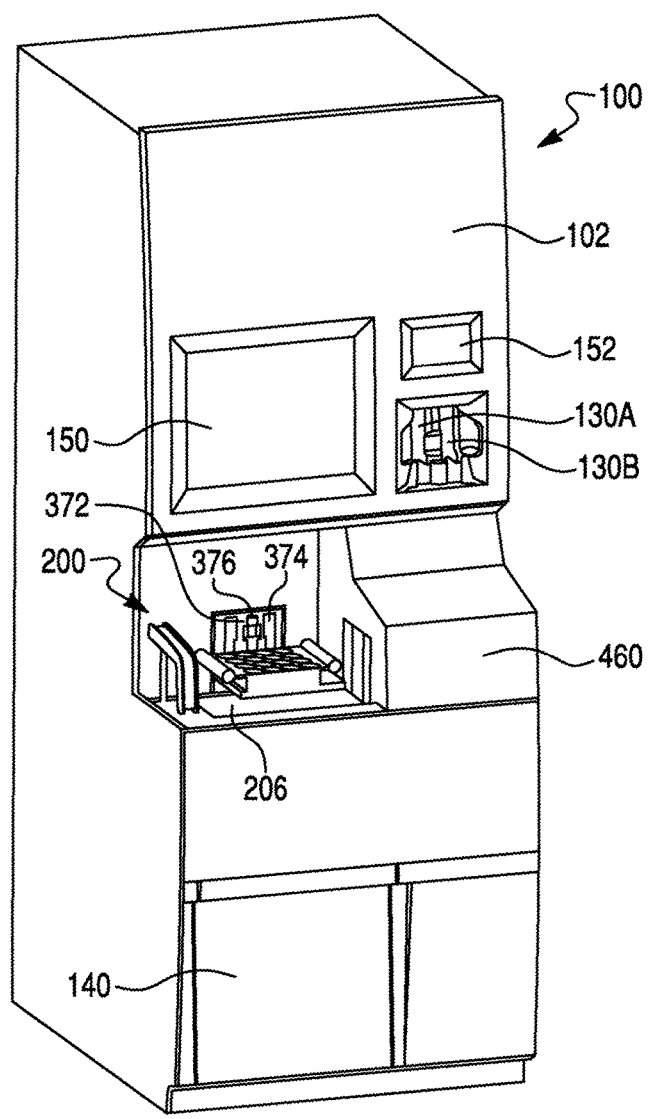
FIG. 29 shows a perspective view of another possible configuration for the detection system.

As shown in FIGS. 28A-29, the carrier 350 may further comprise a pair of alignment arms 368A and 368B and a release tab 370 operable with a release mechanism 372 for releasing the specimen containers 500 at an automated loading mechanism 200 of a detection system 100. The release mechanism 372 comprises a pair of slots 374 that correspond to the pair of alignment arms 368A and 368B, to ensure the carrier 350 is properly aligned at the loading station or area 202 for depositing the specimen containers 500, and a release bar 376. In operation, a technician transports a carrier 350, containing one or more specimen containers 500, to the automated loading mechanism 200 and presses the carrier 350 against the release bar 376, with the alignment arms 368A and 368B aligned with the corresponding slots 374 of the release mechanism 372. By pressing the carrier 350 against the release bar 376, the release tab 370 is pushed in or depressed, thereby moving the slide plate 362 to the "open" position and allowing the specimen containers 500 to fall out of the through holes 360 and onto the loading station or area 202. The technician can then lift the carrier 350 upward until the carrier body 351 and plurality of through holes 360 clear the specimen containers 500, thereby depositing the containers at the automated loading mechanism 200 for automated loading into the detection system 100. As one of skill in the art would appreciate other design configurations are possible.

As shown in FIGS. 1-3, the loading station or area 202 is typically an easily accessible location or area of the automated loading mechanism 200 where a user or technician can place one or more specimen containers 500 for loading into the detection system 100. Once at the loading station 202, the containers 500 will be transported, using a transport mechanism 204, from the loading station or area 202 to an entrance location or port 110, and subsequently through the entrance location or port 110 and into the detection system 100. Accordingly, a user or technician can simply place one or more specimen containers 500 at the loading station or area 202 and walk away, while the containers 500 are automatically loaded into the detection system 100. Once the specimen containers 500 have been transported into the system, they can be moved to one or more work-flow stations using a container management device or locator device, and/or transferred to a holding structure or rack, as described elsewhere herein.

In one embodiment, as shown in FIGS. 1-3, 5A and 5B, the transport mechanism 204 is a conveyor belt 206 operable to transport (e.g., convey) the containers 500 to an entrance location or port 110 and subsequently through the entrance location or port 110 and into the detection system 100. However, other means or mechanisms for transporting the specimen containers 500 from the loading station or area 202 to the entrance location or port 110 are envisioned, and may include, but are not limited to, feed screws, timing belts having grooves or molded plates, and the like. In other embodiments, the process of automated loading of a specimen container 500 into the detection system 100 may further comprise transferring the container to a holding structure or rack using a transfer mechanism 650 or moving the container to one or more work-flow stations using a container locator device (see, e.g., FIG. 24, 400A), as described below.

As shown in FIGS. 1-3, 5A and 5B, the loading station or area 202 and transport mechanism 204 comprise a conveyor belt 206. In accordance with this embodiment, the user or technician can place one or more specimen containers 500 at a specific location or area (i.e., the loading station or area 202) of the conveyor belt 206 for automated loading of the containers 500 into the detection system 100. The conveyor belt 206 may run continuously, or may be activated by the physical presence of the container 500 at the loading station or area 202. For example, a system controller can be used to operate the conveyor belt 206 (i.e., turn it on or off) based on a signal (e.g., a light sensor) indicating the presence, or absence, of one or more specimen containers at the loading station 202. Similarly, one or more sensors can be used at the entrance location or port 110 to indicate if a container is improperly loaded and/or has fallen over and may cause jamming The conveyor belt 206 operates to move or transport the containers 500 from the loading station or area 202 (e.g., the left portion of the conveyor belt 206, as shown in FIG. 1) to the entrance location or port 110, thereby accumulating one or more containers 500 at the entrance location or port 110 to be loaded into the detection system 100. Typically, as shown in FIGS. 1-3 and 5A-5B, the loading station or area 202, transport mechanism 204 or conveyor belt 206, and entrance location or port 110 are located outside, or on the housing 102 of the detection system 100. In one embodiment, the automated loading mechanism 200 is located on a shelf 180 located on top of the lower section 170 and adjacent to the upper section 160 of the system 100. Also, as shown, the transport mechanism or conveyor belt 206 typically operates in a horizontal plane, so as to maintain the specimen containers 500 in a vertical or up-right orientation (i.e., such that the top portion 506 of the container 500 is up) for loading into the detection system 100 (see, e.g., FIGS. 1-3 and 5A-5B). As shown in FIGS. 1-3, the transport mechanism or conveyor belt 206 moves, for example, from left-to-right, or from the loading station or area 202 towards the entrance location or port 110, to transport one or more free standing containers 500 (see, e.g., FIG. 2, arrow 208).

In one embodiment, as shown, for example in FIGS. 1-3 and 10-11, the automated loading mechanism 200 will further comprise one or more guide rails 210 located juxtaposed to one or both sides of the transport mechanism or conveyor belt 206. The one or more guide rails 210 function to guide or direct the specimen containers 500 to the entrance location or port 110 during operation of the transport mechanism or conveyor belt 206. In one embodiment, the guide rails operate to funnel or guide the specimen containers into a single file line at the back of the automated loading mechanism 200, where they await their turn to be loaded, one container at a time, into the detection system 100. In another design aspect, as shown for example in FIG. 22, the detection system 100 may further comprise a locator device cover 460 that covers a locator device (described elsewhere herein) and encloses an interior locator device chamber (not shown) therein. The locator device cover 460 may comprise one or more container guide rails 462 for guiding a specimen container 500, as it is transported from the automated loading mechanism 200 to the entrance location or port 110, and subsequently into the interior chamber, thereby automatically loading the specimen contain into the system. In accordance with this embodiment, the interior locator device chamber (not shown) is considered to be a part of the interior chamber, which is described elsewhere herein.

In still another embodiment, the automated loading mechanism 200 may further comprise a means or device for reading or otherwise identifying the specimen containers 500 as the containers enter the detection system 100. For example, the containers 500 may include a bar code label 508 which can be read for container identification and tracking within the system. In accordance with this embodiment, the detection system 100 will include one or more bar code readers (see, e.g., 410 in FIGS. 14-15) at one or more locations within the system. For example, the detection system 100 may include a bar code reader at the entrance location or port 110 to read, identify and log the individual containers 500 into the detection system controller as they enter the system. In another embodiment, the entrance location or port 110 may also include a means or device (e.g., a container rotator or rotating turntable, as described elsewhere herein) for rotating the container within the entrance location or port 110 to enable reading of the bar code label 508. In another possible embodiment, the transfer mechanism (see, e.g., FIG. 5B, 650) may rotate the container 500 to enable reading of the bar code label 508. Once the bar code has been read, the transfer mechanism will typically transfer the container 500 from the entrance location or port 110 to one of a plurality of receiving structures or wells 602 in one of a plurality of holding structures or racks 600.

In yet another embodiment, if the bar code 508 cannot be properly read, (e.g., the label is misread or a reading error occurs) the detection system controller (not shown) can direct the container 500 to a misread/error location or port 120 for user access to the unreadable or misread container 500. The user can re-load the container using the automated loading mechanism 200 and/or at the user's discretion, may optionally manually load the container 500 and hand enter container 500 information into the system controller (e.g., using the user interface 150). In another embodiment, the detection system 100 may contain a high priority (or STAT) loading location (not shown) for the loading of high priority containers and/or for manual loading of containers where the label has been misread or a reading error has occurred.

Figure 10:
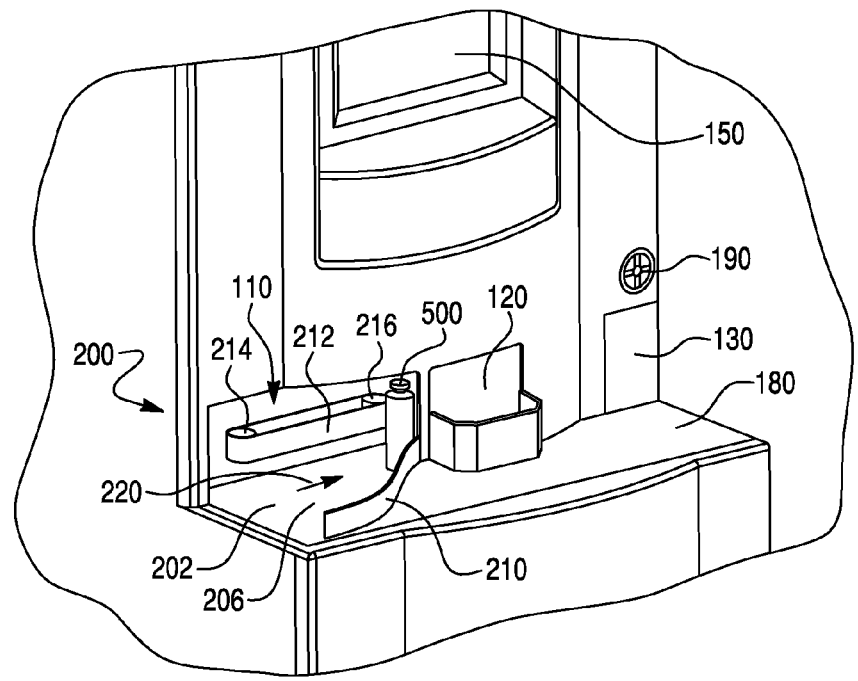
FIG. 10 is a perspective view of another configuration of the automated loading mechanism, showing a first conveyor belt operable in a horizontal plane and a second conveyor belt operable in a vertical plane.

Another design configuration of the automated loading mechanism is shown in FIG. 10. As shown in FIG. 10, the automated loading mechanism 200 comprises a loading station or area 202, a first conveyor belt 206, and an entrance location or port 110. The conveyor belt 206 operates to transport the specimen containers 500 from the left edge of the system 100 (i.e., the location of the loading station 202) to the entrance location or port 110. In this example, the movement is from left-to-right and is represented by arrow 220 in FIG. 10. The automated loading mechanism 200 may further comprise a guide rail 210 and a second conveyor belt 212, which operates around a set of gears or wheels 214, 216. In accordance with this embodiment, the second conveyor belt 212 is orientated and operable in a vertical plane above the first horizontal conveyor belt 206, and can operate in a clockwise or counter-clockwise manner (i.e., to move the belt from left-to-right or from right-to-left). The clockwise or counter-clockwise operation of the second vertically orientated conveyor belt 212 can provide the specimen container 500 with a counter-clockwise or clockwise rotation, respectively, about a vertical axis of the container. Applicants have found that providing a specimen container 500 with clockwise or counter-clockwise rotation can prevent and/or reduce jamming or clogging of the automated loading mechanism 200 as a plurality of specimen containers 500 accumulate at the entrance location or port 110. Once the containers 500 have arrived at the entrance location or port 110 they can be moved into the detection system 100.

In still another embodiment, the automated loading mechanism 200 may also contain a backer board (not shown) located in a horizontal plane underneath the first conveyor belt 206. As one of skill in the art would appreciate, the conveyor belt 206 may have some give, flexibility, or may otherwise be considered "springy". This springy nature of the conveyor belt 206 may lead to instability of the specimen container 500 as the container is transported across the conveyor belt 206 from the loading station or area 202 to the first port or entrance location 110 and may result in specimen containers 500 tipping or falling over. Applicants have found that by including a rigid or semi-rigid backer board underneath the conveyor belt 206, this problem can be reduce and/or eliminate altogether, thereby, reducing and/or preventing jamming or clogging of the loading mechanism 200 (e.g., with containers 500 that have fallen over). In general, any known backer board material may be used. For example, the backer board can be a rigid or semi-rigid board made of plastic, wood, or metal.

Figure 11:
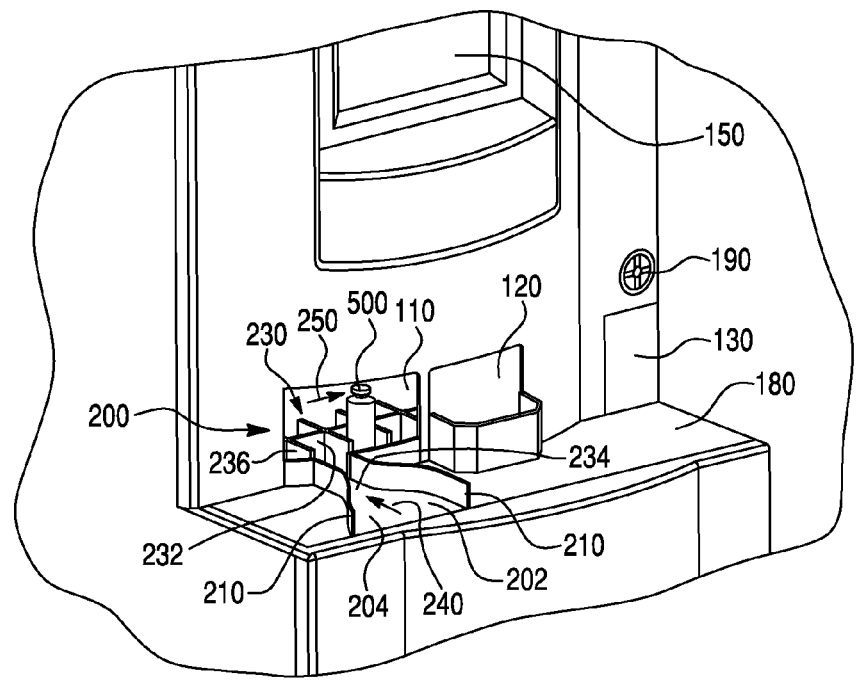
FIG. 11 is a perspective view of yet another configuration of the automated loading mechanism, showing a first conveyor belt operable in a horizontal plane and a second conveyor belt having a plurality of paddles and operable in a vertical plane.

Yet another configuration of the automated loading mechanism is shown in FIG. 11. As shown in FIG. 11, the automated loading mechanism 200 may comprise a loading station or area 202, a conveyor belt 206, and an entrance location or port 110. Also as shown, the conveyor belt 206 can operate to transport the specimen containers 500 from the front edge of the system 100 (i.e., the loading station 202) to the entrance location or port 110. In this example, the movement of the loading mechanism 200 is from front-to-back (i.e., from the front edge of the instrument to the loading port 110) and is represented by arrow 240 in FIG. 11. As shown, the automated loading mechanism 200 may further comprise one or more guide rails 210 to guide the one or more specimen containers 500 to the entrance location or port 110, as they are transported by the conveyor belt 206.

Optionally, as shown in FIG. 11, the automated loading mechanism 200, in accordance with this embodiment, may include a second transport mechanism 230. In one embodiment, the second transport mechanism 230 may comprise a second conveyor belt 232 located in, and operable in, a vertical plan above the first conveyor belt 206. As shown, the second transport mechanism 230 may further comprise a plurality of paddles or plates 236 attached to the second conveyor belt 232. In accordance with this embodiment, the first conveyor belt 206 operates to move or transport one or more specimen containers 500 from the loading station or area 202 to the second transport mechanism 230, where the containers 500 are individually moved or transported into a well or space 234 between the paddles or plates 236. The second conveyor belt 232 operates around a set of gears or drive wheels (not shown), and runs or moves, for example, from left-to-right across the back edge of the automated loading mechanism 200, thereby transporting the containers 500 from left-to-right along the back of the loading mechanism 200 and to the entrance location or port 110 (see, e.g., arrow 250). Once the containers 500 have arrived at the entrance location or port 110 they can be moved into the detection system 100.

Figure 12:
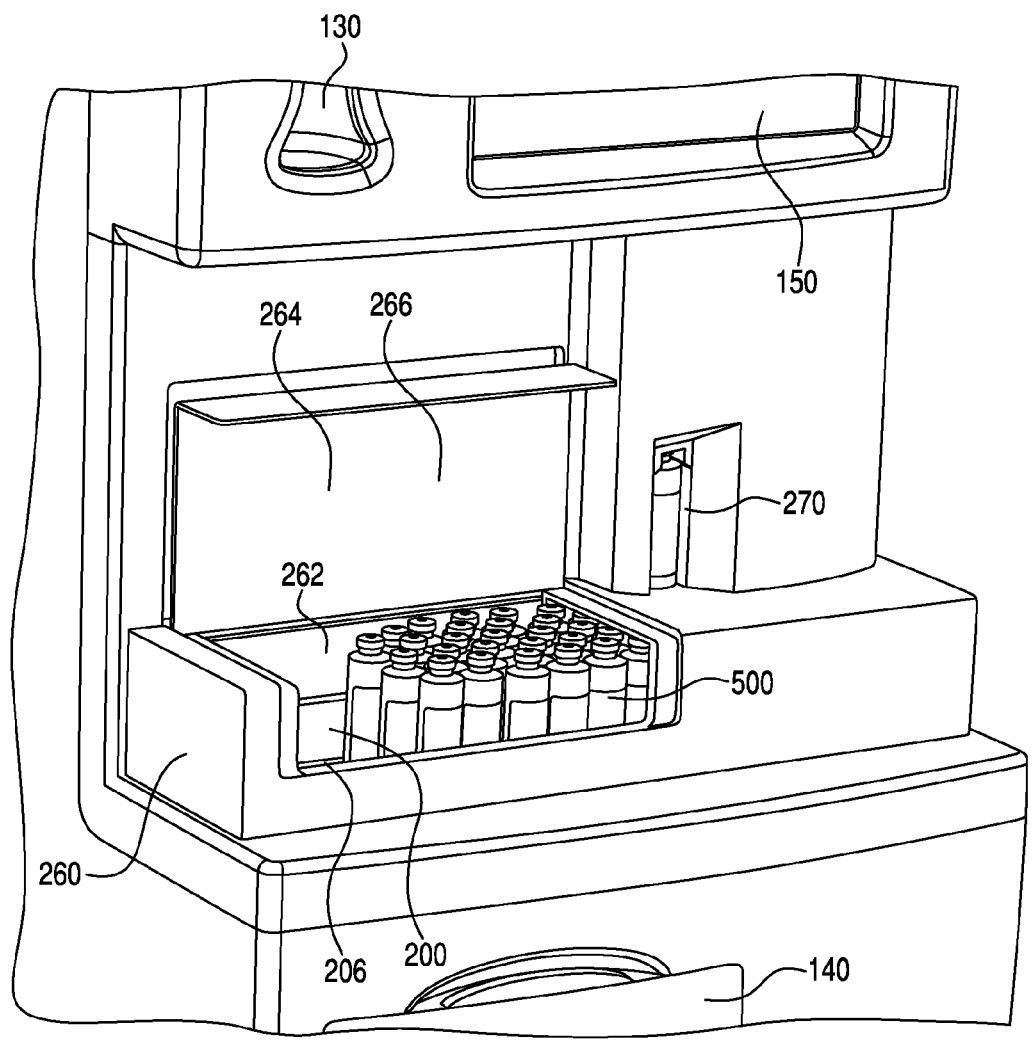
FIG. 12 is a perspective view of a casing and cover provided with an automated loading mechanism.

In yet another embodiment, the automated loading mechanism 200 can be enclosed or encased in a protective housing or casing 260, as shown for example in FIG. 12. In accordance with this embodiment, the automated loading mechanism 200, or one or more components thereof (i.e., one or more of the loading area, transport means (e.g., conveyor belt 206) and/or entrance location or port (not shown)), can be housed or encased in a protective housing or casing 260. The protective housing or casing 260 will have an opening 262 providing access to, and for loading specimen container 500 into/onto the automated loading mechanism 200 housed therein. Optionally, the protective housing or casing 260 can further include a cover means 264 that can be closed or shut to protect the automated loading mechanism 200, and/or containers 500, contained therein. The cover can be a closable lid 266, as shown, or other structure or means for closing the housing or casing 260. For example, in another embodiment, the cover 264 can be a lightweight curtain (not shown) that can be pulled shut over the opening 262. The protective housing or casing 260 may also provide a priority container loading port 270 for the loading or high priority containers (i.e., STAT container) and/or misread containers. In one embodiment, a container 500 can be manually loaded into the priority port 270.

Another embodiment of an automated loading mechanism is shown in FIGS. 13-15. Like the previously described automated loading mechanism, the automated loading mechanism 300 shown in FIGS. 13-15, comprises a container loading station or area 302, a transport mechanism 304 and a container entrance location 306, for the fully automated loading of one or more specimen containers 500 into the detection system 100.

Figure 17:
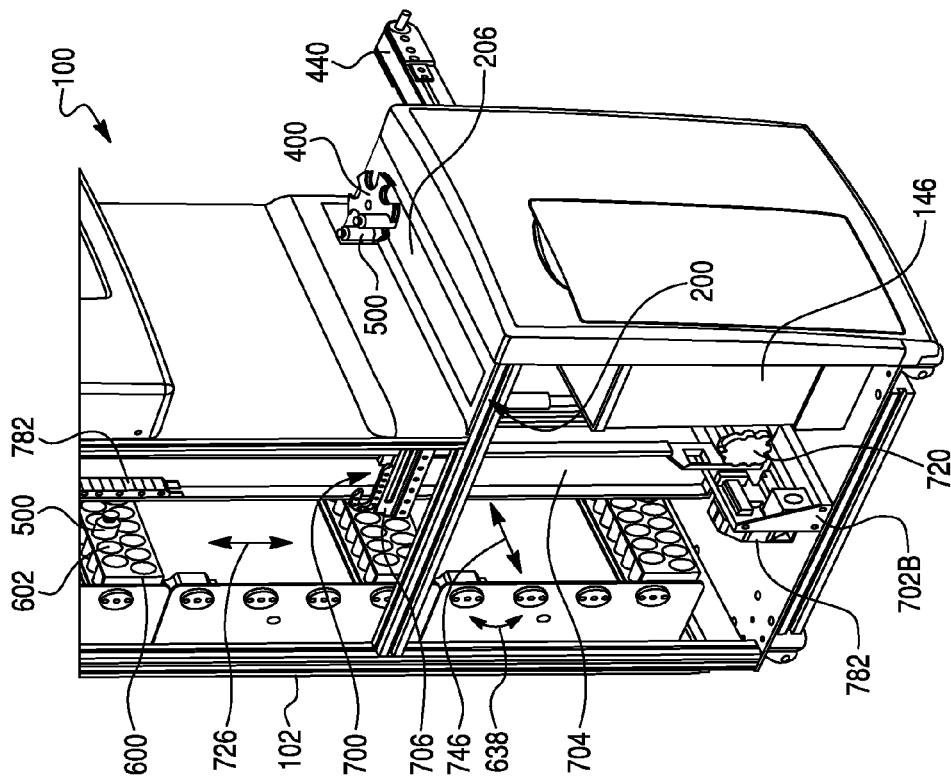
FIG. 17 is a perspective view of the automated detection apparatus comprising the automated loading mechanism shown in FIG. 14. The container loading area of the automated loading mechanism is shown in a user accessible location on the front of an automated system for rapid non-invasive detection of a microbial agent. The automated detection system and the container loading area are shown with side panels removed and/or as see through features to reveal other features, as described herein.

The container loading area 302 is in an easily accessible location on the detection system 100 to allow a user to easily place one or more specimen containers 500 therein, as shown for example in FIG. 17. In accordance with this embodiment, the specimen containers 500 are loaded in a horizontal orientation, such that they are lying on their side, as shown for example in FIG. 13. Once at the container loading area 302, the specimen containers 500 can be transported by a transport mechanism 304 from the container loading area 302 to an entrance location 306, from where the containers 500 will enter the detection system 100, as described in more detail herein. Surprisingly, regardless of the specimen container 500 orientation in the loading area 302 (i.e., regardless of whether the top portion 506 of the container 500 is facing the detection system 100 or facing away from the detection system 100 (as shown, e.g., in FIG. 14)), the automated loading mechanism 300 of this embodiment is capable of loading the specimen containers 500 into the detection system 100.

In one embodiment, the container loading station or area 302 comprises a loading reservoir 303 that is capable of holding one or more specimen containers 500, as shown for example in FIG. 13. The loading reservoir 303 can be designed to hold from 1 to 100 specimen containers, from 1 to 80 specimen containers, or from 1 to 50 specimen containers. In other design concepts, the loading reservoir may hold 100 or more specimen containers 500. The automated loading mechanism 300 of this embodiment may further comprise a lid or cover (not shown), which the user or technician can optionally close to cover the loading reservoir 303 and loading area 302. Various designs are possible and contemplated for the lid or cover.

As show in FIGS. 13-14, the loading reservoir 303 contains a transport mechanism 304, for example, a sloped ramp that slopes downwards towards an entrance location 306 so as to transport the specimen containers 500 from the loading area 302 to the entrance location 306. In accordance with this embodiment, the sloped ramp will allow the specimen containers to roll or slide down the ramp to the entrance location 306. Although, a sloped ramp is exemplified in the figures other designs are possible and contemplated for the transport means or mechanism 304 for transporting the specimen containers to the entrance location 306. For example, in one alternative design concept the transport mechanism 304 may comprise a conveyor belt (not shown). In accordance with this design concept the conveyor belt can be designed to hold one or more specimen containers and may optionally be designed such that the conveyor belt slopes downward towards the entrance location 306.

Once at the entrance location 306, a drum or drum-like loading device 308 will be used for loading the specimen containers 500 into the detection system 100. As shown, the drum-like loading device 308 has one or more horizontally orientated slots 310 for holding one or more specimen containers therein. Each individual slot 310 is capable of holding a single specimen container 500. In one embodiment, the drum-like loading device 308 has a plurality of slots, for example, from 1 to 10 slots, from 1 to 8 slots, from 1 to 6 slots, from 1 to 5 slots, from 1 to 4 slots, or from 1 to 3 slots for holding specimen containers 500 therein. In another embodiment, the drum-like loading device 308 can be designed to have a single slot capable of holding a single specimen container 500 therein.

The drum-like loading device 308 is capable of rotating (either in a clock-wise direction, or counter-clock wise direction) about a horizontal axis, and is capable of picking-up and loading individual specimen container 500 into the detection system 100. In operation, the rotation of the drum or drum-like loading device 308 picks up a horizontally orientated specimen container 500 in one of a plurality of horizontally orientated slots 310, and moves the container 500, by rotation of the drum or drum-like loading device to a tumbler device 330 (see, e.g., FIG. 16). Any known means in the art can be used for rotation of the drum or drum-like loading device 308. For example, the system may employ the use of a motor (not shown) and drive belt 316 for rotation of the drum-like loading device 308.

In another embodiment, as shown in FIG. 13, the automated loading mechanism 300 of this embodiment may further comprise a single container loading port 312. In operation, a user or technician can place a single specimen container into the single container loading port 312 for quick, or immediate loading, for example of a STAT specimen container. Once placed in the single container loading port 312, the container will drop or fall via gravity onto a second transport mechanism 314, for example, a sloped ramp that slopes downward toward the drum-like loading device 308 for quick or immediate automated loading of the specimen container into the detection system 100.

As shown in FIGS. 13-16, the drum or drum-like loading device 308 rotates in a vertical plane (i.e., around or about a horizontal axis) to move the specimen container 500 from the entrance location 306 to a tumbler device 330. The tumbler device comprises an open slot at the top of a vertically orientated chute 332. Once moved to the tumbler device 330, the specimen containers are up-righted (i.e., the specimen containers are re-positioned from a horizontal container orientation to an up-right vertical container orientation) by a cam mechanism and vertically orientated chute 332. In operation, the cam mechanism (not shown) is capable of sensing the top and/or bottom of the specimen container, and pushing the specimen container 500 in a horizontal direction from the base of the specimen container, thereby allowing the base to drop or fall through the opening of a vertically orientated chute 332. Accordingly, the tumbler device 330 operates to allow the container 500 to drop (via gravity) bottom first through the vertical chute 332 and into a first locator well of a container locator device 400 (described elsewhere herein), thereby re-orienting the container 500 in a vertical, up-right orientation.

Figure 16:
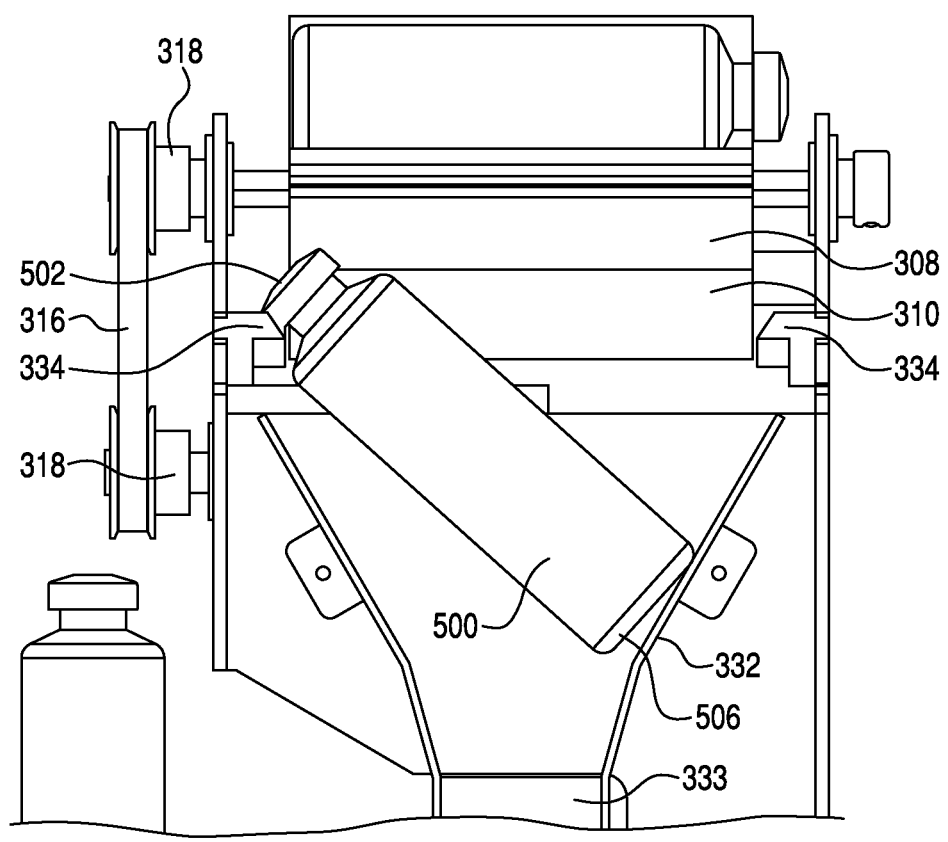
FIG. 16 is a cross-sectional view of the automated loading mechanism shown in FIGS. 14-15. More specifically.

As shown for example in FIG. 16, the tumbler device 330 has two tapered ledges 334, one on each side of the drum, each being narrow at a front edge and thicker at a back edge. The ledges 334 are aligned so that the cap portion 502 of the container 500 will be caught or held by the ledge (i.e., the cap will move over the top side of the ledge such that the cap will rest on the top of ledge 334) as the drum rotates. The ledge 334 only holds the cap portion 502 of the container 500 in place briefly, as the bottom of the container falls through the vertical chute 332. Furthermore, the bottom or base 506 of the container will not be caught or held by the ledge. Instead, the tapered ledge 334 will act to push or slide the bottom or base 506 of the container 500 in a horizontal direction, from the bottom 506 of the container 500 towards the top or cap portion 502 of the container (see FIG. 4), as the drum or drum-like loading device 308 rotates. This action helps to ensure that the cap end 502 of the container is held by the top edge of the ledge 334, thereby allowing the bottom 506 of the container 500 to fall freely through the vertical chute 332 and into the container locator device 400. By having a ledge 334 on each side of the drum or drum-like loading device 308, container 500 orientation in the rotating drum in not essential. The container 500 will be up-right by the tumbler device 330 regardless of whether the cap end 502 of the container is on the right or left side (see, e.g., FIG. 16) of the drum-like loading device 308, as the corresponding ledges 334 will function to hold the cap or top 502 of the container as the bottom 506 falls through the vertical chute 332. In another embodiment, the vertical cute 332 may further comprise a narrower section 333 that helps direct the falling container 500 into the container locating device 400. In operation, as the drum or drum-like loading device 308 rotates over the open slot at the top of the vertically orientated chute 332, the cap or top portion 502 of the container 500 is held at the outer edge of the drum by one or more ledges 334 (see, e.g., FIG. 16). The ledges 334 hold the cap or top portion 502 of the container 500 in place while allowing the bottom 506 of the container to swing or fall freely out of the drum or drum-like loading device 308 and into the vertically orientated chute 332, thereby up-righting or vertically orientating the container 500 as it drops or falls via gravity through the vertically orientated chute 332 bottom first, as previously described.

Container Management Means or Locator Device

As shown, for example in FIGS. 13-15, 18, and 25A-25C the detection system 100 may further comprise a container management device or locator device 400. The container management device or locator device 400 can be used to manage, move or otherwise locate a container 500, once inside the housing 102 of the detection system 100, among various work-flow stations 404. In one embodiment, the container management device or locator device 400 can be used in combination with the automated loading mechanism 300 shown in FIGS. 13-15, as shown. In another embodiment, the container management device or locator device 400 can be used in combination with the automated loading mechanism 200 shown, for example, in FIG. 18. The container management device or locator device 400 in FIGS. 13-15 and 18 is shown schematically and the parts not to scale.

Figure 24:
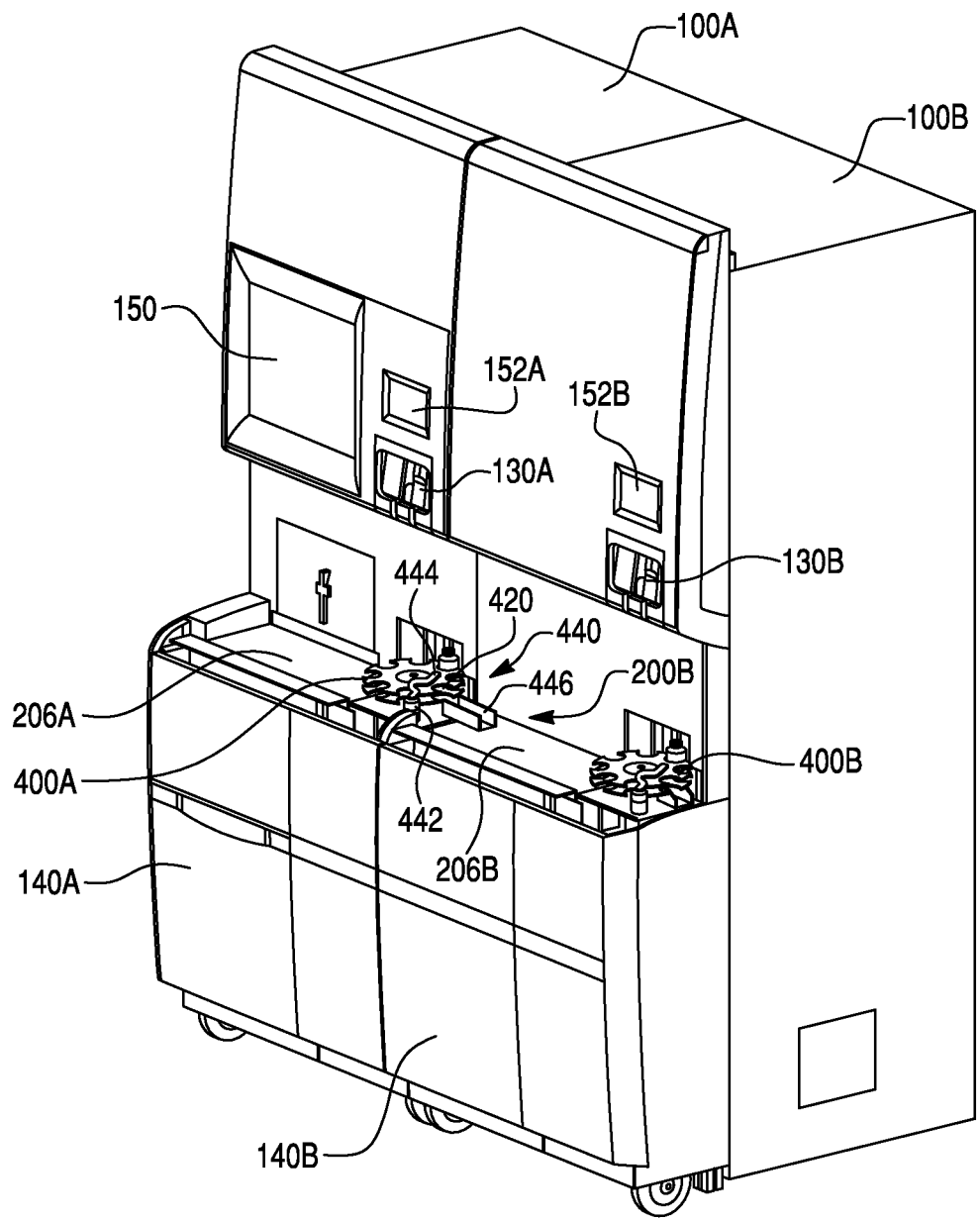
FIG. 24 is a perspective view of yet another embodiment of the automated detection system. As shown, the automated detection system comprises a first detection apparatus having an automated loading mechanism and a second or down-stream detection apparatus linked or "daisy-chained" to the first detection apparatus, as described herein.

The container management device or locator device 400 comprises a rotatable wheel-like device or rotatable disk that contains one or more locator wells 402, for example 1 to 10 locator wells, 1 to 8 locator wells, 1 to 5 locator wells, 1 to 4 locator wells, or 1 to 3 locator wells 402. In one embodiment, the locator device comprises opposable parallel plates or discs (see, e.g., FIGS. 25A-25C). Each individual locator well 402 is capable of holding a single specimen container 500. In operation, the locator device 400 rotates (either clock-wise or counter clock-wise) in a horizontal plane (and around or about a vertical axis) to move an individual container 500 to or among various work-flow stations 404 (i.e., from station-to-station). In one embodiment, the work-flow station 404 is operable to obtain one or more measurements or readings of the specimen container, thereby providing information about the container, such as, container lot number, container expiration date, patient information, sample type, fill level, etc. In another embodiment, the one or more work-flow stations 404 may comprise one or more container management stations, such as, a container pick-up station or a container transfer station. For example, the locator device 400 is capable of moving an individual specimen container 500 to one or more work-flow stations 404, such as: (1) a bar code reading station; (2) a container scanning stations; (3) a container imaging station; (4) a container weighing station; (4) container pick-up station; and/or (5) a container transfer station. In another embodiment, one or more of these measurements and/or readings can occur at the same station. For example, container weight, scanning, imaging and/or pick-up may occur at a single station location. In yet another embodiment, the detection system may contain a separate pick-up station. A container can be picked-up by a transfer mechanism (as described herein) at the pick-up location, and transferred to other locations (e.g., to a holding structure and/or agitation assembly) within the detection system 100. In still another embodiment, the detection system 100 may contain a transfer station for the transfer of a specimen container 500 to another instrument, e.g., a second automated detection instrument. In accordance with this embodiment, the transfer station may communicate with a system transfer device 440. For example, as shown, the system transfer device 440 may be a conveyor belt that allows the specimen container to be transferred to another location within the detection system 100, or in another embodiment, to another instrument (e.g., a second detection system (e.g., as shown in FIG. 24)). As shown in FIG. 14-15, the locator device 400 comprises: (1) an entrance station 412; (2) a bar code reading and/or scanning station 414; (3) a container weighing station 416; (4) a container pick-up station 418; and (5) a system transfer station 420 for transfer of the container to another instrument. The locator device may further comprise a rotatable turntable device 406, for rotating a container to facilitate bar code reading and/or container scanning, and/or a scale or weighing device 408, for weighing a container.

As previously described, in operation, the container management device or locator device 400, operates to move or otherwise locate a given specimen container 500 to a given work-flow station 404. In one embodiment, these work-flow stations 404 are included within the housing 102 of the detection system 100. For example, as shown in FIGS. 13-15 and 18, an automated loading mechanism can deposit or place a specimen container 500 into a locator well 402, as described elsewhere herein. The container management means or locating device 400 can then rotate to move or locate the specimen container among various work-flow stations within the system, such as for example, a bar code reading station, a container scanning stations, a container imaging station, a container weighing station, container pick-up station, and/or a container transfer station.

Transfer Means or Mechanism

As shown, for example in FIGS. 5-9B and 17-21, the automated detection system 100 may further comprise an automated transfer means or mechanism operable for the transfer of a specimen container 500, and/or for container management, within the system. As already described, the entrance location or port 110 receives containers from, for example, a conveyor system 206 shown best in FIGS. 1-3. As the containers accumulate in the entrance location or port 110, the containers are moved within the detection system 100 whereby a transfer mechanism (e.g., a robotic transfer arm with a container gripping means) can pick-up, or otherwise receive, an individual specimen container 500 and transfer and place that container into a holding structure or rack 600 within the detection system 100, as described in more detail herein. As known in the art, the transfer mechanism may use a vision system (e.g., camera), pre-programmed dimensional coordinates and/or precision motion controlling to transfer a specimen container to, and load the specimen container into, the holding structure or rack 600.

As shown in FIGS. 1-3 and 13-15, specimen containers 500 are loaded into, and/or transported within, the detection system 100 using an automated loading mechanism 200 (FIG. 1-3) or 300 (FIGS. 13-15). As shown, the containers 500 are typically loaded into the detection system 100 in a vertical orientation (i.e., such that the top or cap portion 502 of the container 500 is up-right). In accordance with one embodiment, the containers 500 are placed or held in a plurality of holding structures or racks 600, and optionally agitated to enhance microorganism growth therein. As shown for example in FIGS. 5A and 5B, the receiving structures or wells 602 of the holding structures or racks 600 can be orientated in a horizontal axis. Accordingly, in accordance with this embodiment, an automated transfer mechanism (see, e.g., FIG. 5B, 650) must re-orientate the container 500, from a vertical orientation to a horizontal orientation, during the transfer of the container 500 from the automated loading mechanism 200, 300 to the receiving structures or wells 602.

In operation, the automated transfer mechanism (e.g., FIG. 5B, 650 or FIG. 20, 700) can operate to transfer or otherwise move, or relocate, a specimen container 500 within the interior chamber 620 of the detection system 100. For example, in one embodiment, the transfer mechanism can transfer a specimen container 500 from an entrance location or port 110 to one of a plurality of holding structures or racks 600. In another embodiment, the transfer mechanism can pick-up a specimen container 500 from a well 402 of the container locator device 400 and transfer the container to a holding structure or well 602 of the holding structure or rack 600. The transfer mechanism can operate to place the container 500 in one of a plurality of container receiving structures or wells 602 that are located in one of a plurality of holding structures or racks 600. In another embodiment, the transfer mechanism can operate to remove or unload "positive" and "negative" containers from the holding structures or racks 600. This automated unloading mechanism can operate to ensure that once a "positive" or "negative" reading has been made for each specimen container 500, the container 500 is removed from the container receiving structures or well 602, making room for another container to be loaded into the detection system 100, thereby increasing system through-put.

In one embodiment, the transfer mechanism can be a robotic transfer arm. In general, any type of robotic transfer arm known in the art can be used. For example, the robotic transfer arm can be a multi-axis robotic arm (for example, a 2-, 3-, 4-, 5-, or 6-axis robotic arm). The robotic transfer arm can operate to pick-up and transfer a specimen container 500 (e.g., a blood culture bottle) from an entrance location or port 110 to one of a plurality of container receiving structures or wells 602 located in one of a plurality of holding structures or racks 600 (optionally having an agitation assembly). Furthermore, to facilitate the necessary movements of the transfer mechanism or robotic transfer arm, the interior chamber 620 of the detection system 100, may includes one or more supports for the robotic transfer arm. For example, one or more vertical supports and/or one or more horizontal supports may be provided. The transfer mechanism or robotic transfer arm will slide up and down and across the supports as necessary to access any of the receiving structures or wells 602 of the holding structures or racks 600. As previously described, the robotic transfer arm can operate to change the orientation of a specimen container from a vertical orientation (i.e., up-right orientation such that the top 502 of the container 500 is up) to a horizontal orientation (i.e., such that the container 500 is laying on it's side), for example, to facilitate in container transfer from a loading station or location, and placement within a holding structure and/or agitation assembly.

In one embodiment, the robotic transfer arm is a 2-, or 3-axis robotic arm and will be capable of transferring the container 500 in one or more horizontal axes (for example, the x- and/or z-axes) and optionally a vertical axis (y-axis) to a specific location, such as the container receiving structures or wells 602 described herein. In accordance with this embodiment, a 2-axis robotic arm will allow movement in 2-axes (for example, the x-, and z-axes), whereas a 3-axis robotic arm will allow movement in 3-axes (for example, the x-, y-, and z-axes).

In another embodiment, the 2-, or 3-axis, robotic arm may further employ one or more rotational movements, capable of transferring or moving the specimen container 500 rotationally about one or more axes. This rotational movement may allow the robotic transfer arm to transfer a specimen container 500 from a vertical loading orientation to a horizontal orientation. For example, the robotic transfer arm may employ a rotational movement to move the specimen container rotationally about or around a horizontal axis. This type of robotic transfer arm would be defined as a 3-, or 4-axis robotic arm. For example, a robotic arm that allows movement in one horizontal axis (the x-axis), one vertical axis (e.g., the y-axis) and one rotational axis would be considered a 3-axis robotic arm. Whereas, a robotic arm that allows movement in two horizontal axes (e.g., the x-, and z-, axes), a vertical axis (the y-axis) and one rotational axis would be considered a 4-axis robotic arm. Similarly, a robotic arm that allows movement in a single horizontal axis (e.g., the x-axis), a vertical axis (the y-axis) and two rotational axes would also be considered a 4-axis robotic arm. In yet another embodiment, the robotic transfer arm 700 can be a 4-, 5-, or 6-axis robotic arm, thereby allowing movement in the x-, y-, and z-axes, as well as rotational movement about, or around, one-axis (i.e., a 5-axis robot), two axes (i.e., a 5-axis robotic arm), or all three horizontal (x-, and z-axes) and vertical axes (y-axes) (i.e., a 6-axis robotic arm).

In yet another embodiment, the robotic transfer arm may include one or more devices for obtaining measurements, scans and/or readings of a specimen container 500. For example, the robotic transfer arm may include one or more video cameras, sensors, scanners, and/or bar code readers. In accordance with this embodiment, the video camera, sensor, scanner and/or bar code reader may aid in container location, reading of container labels (e.g., bar codes), container scanning, remote field servicing of the system, and/or detecting for any possible container leaks within the system. In yet another design possibility, the robotic transfer arm may include a UV light source to aid in automated decontamination, if necessary.

Figure 6:
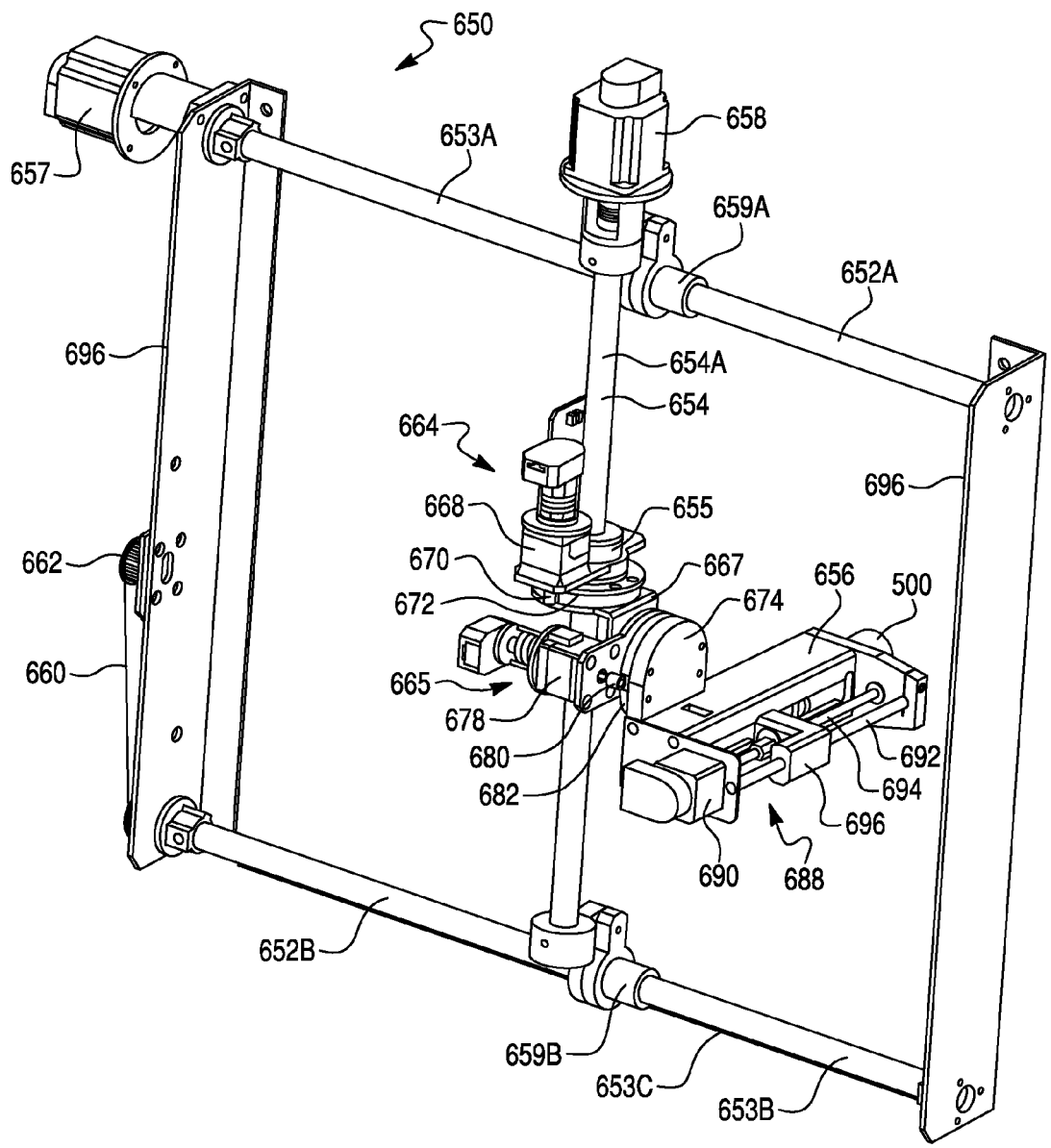
FIG. 6 is a perspective view of the transfer mechanism shown in FIGS. 5A and 5B, showing the horizontal and vertical support rails. Also shown are first and second rotational mechanisms, which are operable to rotate the transfer mechanism about one or more axes.

One design possibility of the transfer mechanism is shown in FIGS. 6-8C. As shown in FIG. 6, the transfer mechanism comprises a robotic transfer arm 650, which comprises an upper horizontal support rail 652A, a lower horizontal support rail 652B, a single vertical support rail 654 and a robotic head 656 that will includes a gripping mechanism (not shown) for picking-up, gripping or otherwise holding a specimen container 500. The transfer mechanism shown in FIGS. 6-8C is shown schematically and the parts not to scale, for example, the horizontal supports 652A, 652B, vertical support and robotic head 656 shown are not to scale. As one of skill in the art would readily appreciate, the horizontal supports 652A, 652B, and vertical support can be increased or decreased in length as needed. As shown, the robotic head 656 is supported by, coupled to, and/or attached to the vertical support rail 654, which in turn is supported by the horizontal support rails 652A and 652B. Also as shown in FIG. 6, the transfer mechanism may comprise one or more mounting supports 696 that can be used to mount the transfer mechanism in the detection system.

In operation, the vertical support rail 654 can be moved along the horizontal support rails 652A and 652B, thereby moving the vertical support rail 654 and the robotic head 656 along a horizontal axis (e.g., the x-axis). In general, any known means in the art can be used to move the vertical support rail 654 along the horizontal support rails 652A and 652B. As shown in FIG. 6, the upper and lower support rails 652A and 652B, can comprise upper and lower threaded shafts (not shown) operable to drive upper and lower horizontal slide blocks 659A and 659B, respectively. Also, as shown in FIG. 6, the upper and lower shafts 652A and 652B can include hollow, elongate reinforcing sleeves 653A, 653B that extends the length of the upper and lower support rails 652A, 652B, and thereby surrounds the upper and lower threaded screws (see, e.g., U.S. Pat. No. 6,467,362). The sleeves 653A, 653B will each further comprise a slot (see, e.g., 653C) in the sleeve 653A, 653B that extends the length of the upper and lower support rails 652A, 652B. Threaded tongues (not shown) are provided that extend through the slot (see, e.g., 653C) and have threads engageable with the threaded shafts (not shown) which are encased in the reinforcing sleeves 653A, 653B. As the threaded shafts (not shown) of the upper and lower support rails 652A, 652B are turned by a first motor 657, the threaded tongues (not shown) moves horizontal slide blocks 659A, 659B along the longitudinal length of the upper and lower support rails 652A, 652B, thereby moving the robotic head 656 along a horizontal axis (e.g., the x-axis) (again, see, e.g., U.S. Pat. No. 6,467,362). A first motor 657 can operate to turn the upper and lower threaded shafts (not shown) and thereby drive upper and lower horizontal slide blocks 659A and 659B (each having internal threads that engage the threaded shafts, respectively) in a horizontal direction along the upper and lower threaded shafts. In one design possibility, the first motor 657 can be used to turn both the upper and lower threaded shafts by including a drive belt 660 and set of pulleys 662 to turn one of the threaded shafts (e.g., the lower threaded shaft) in parallel with the first threaded shaft, as the first threaded shaft is turned by the motor 657.

Figure 7A:
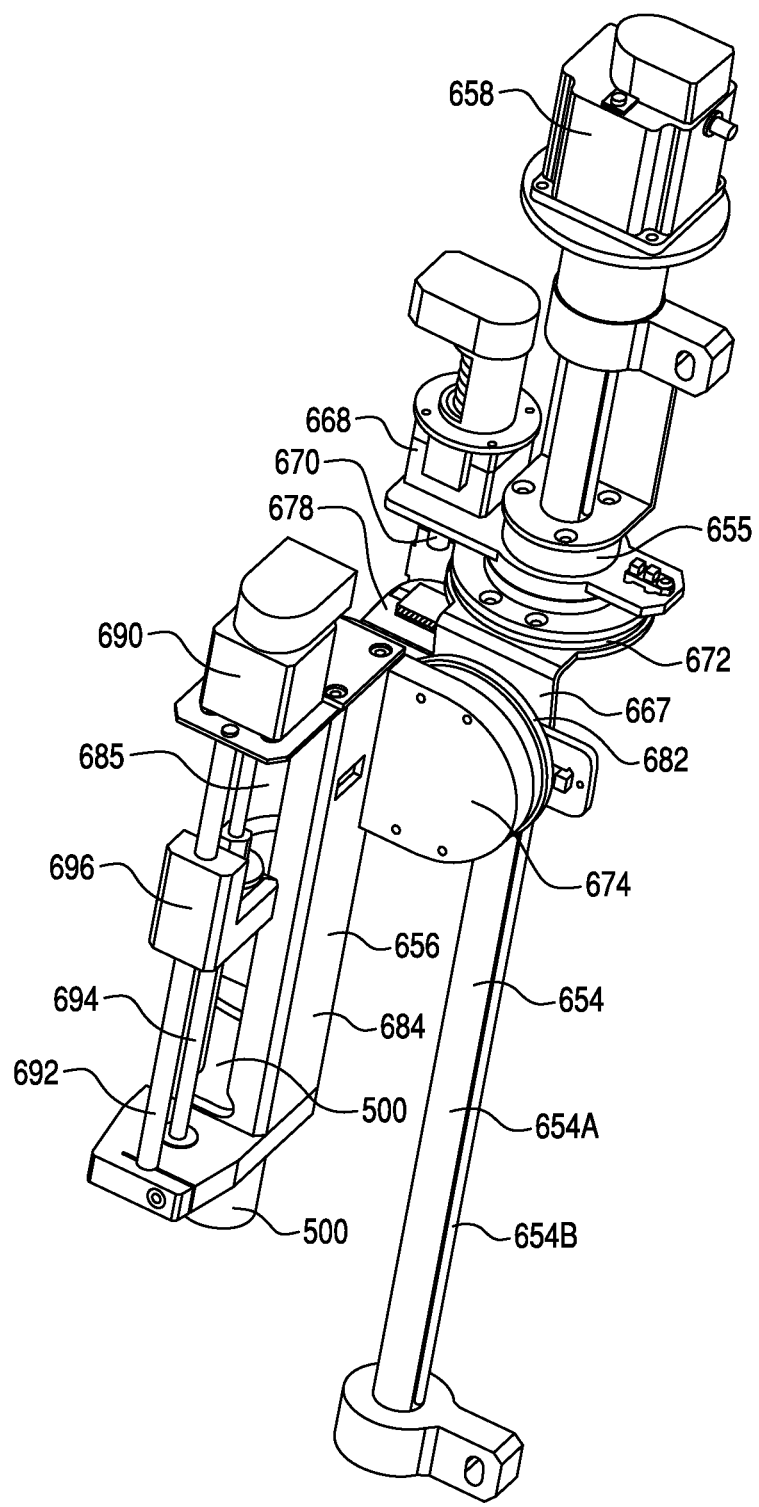
FIG. 7A is a perspective view of the robotic head and vertical support rail shown in FIGS. 5A and 5B.
Figure 7B:
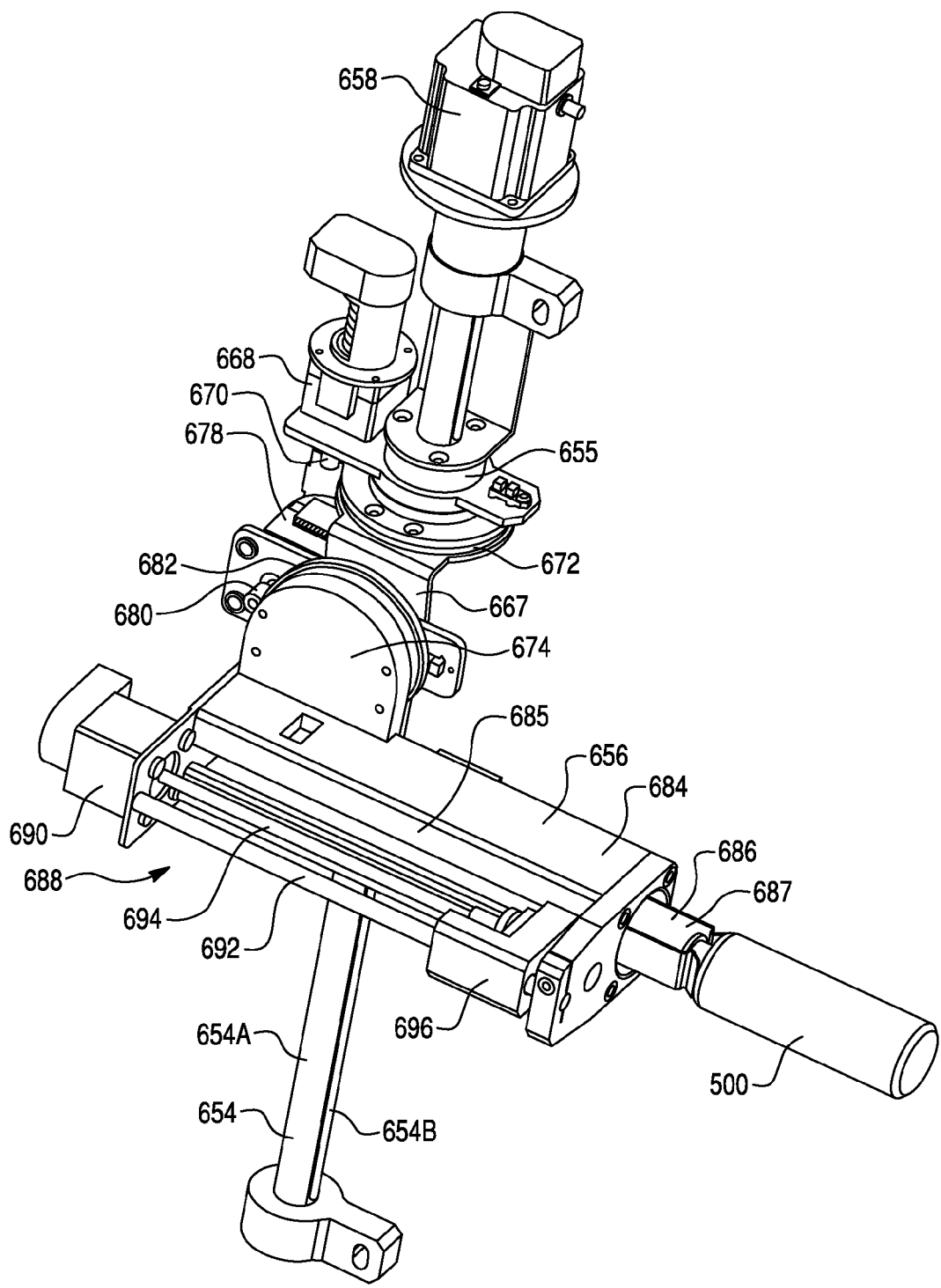
FIG. 7B is another perspective view of the robotic head and vertical support rail shown in FIGS. 5A and 5B.
Figure 8A:
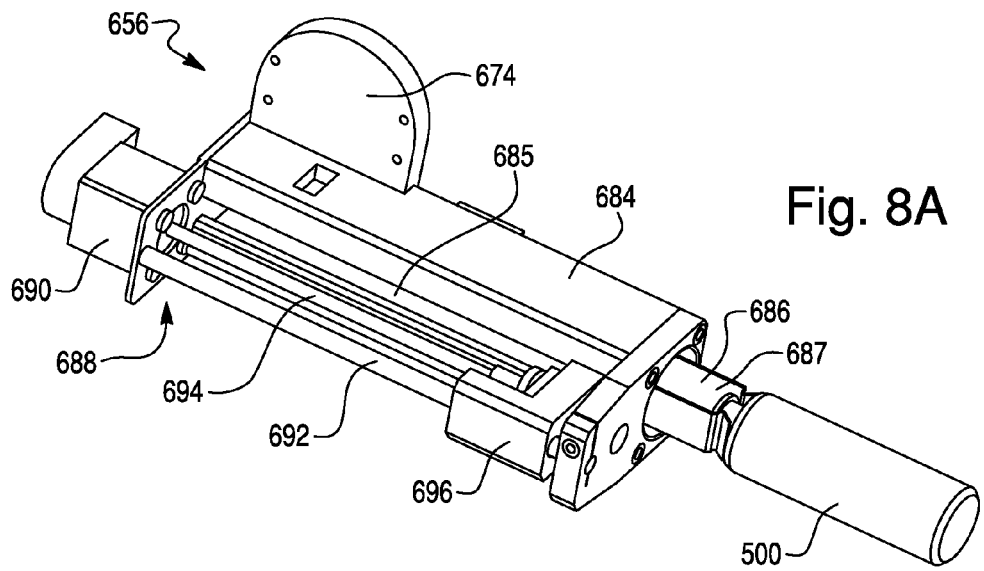
FIGS. 8A-C shows a time-elapsed loading of a specimen container into the holding chamber of the robotic head shown in FIGS. 5A and 5B.
Figure 8B:
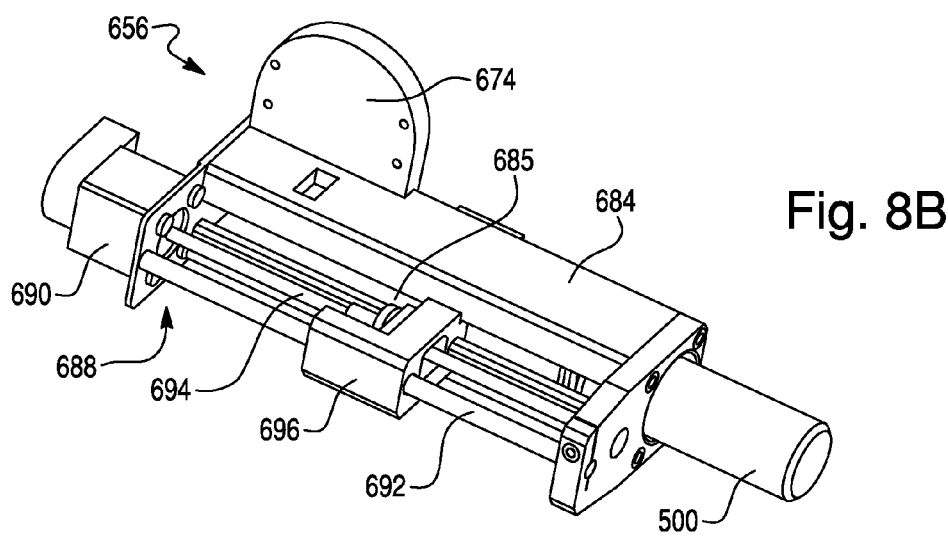
Figure 8C:
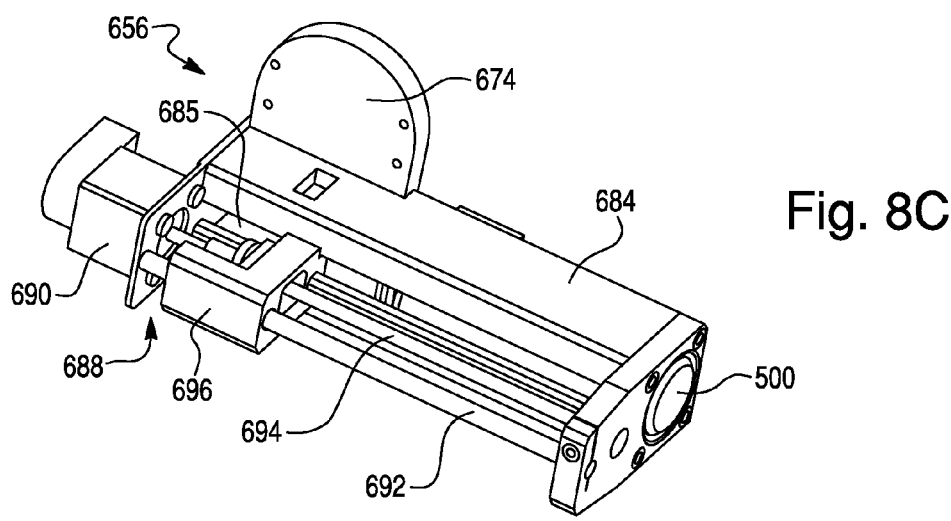

As shown in FIG. 6, the vertical support rail 654 may further comprise a vertical threaded drive shaft (not shown) operable to drive a vertical slide block 655 and thereby move the robotic head 656 along a vertical axis (e.g., the y-axis). In operation, a second motor 658 can operate to turn a vertical threaded shaft (not shown) and thereby drive vertical slide block 655 in a vertical direction along the vertical threaded shaft. In another embodiment, as shown in FIGS. 6-7B, and as described hereinabove, the vertical threaded shaft may further comprise a hollow, elongate reinforcing sleeve 654A that extends the length of the vertical support rail 654, and thereby surrounds the vertical threaded shaft (not shown). The sleeve 654A will further comprise a slot 654B that extends the length of the vertical support rail 654. A threaded tongue (not shown) is provided that extends through the slot (not shown) and has threads engageable with the threaded shaft (not shown). As the threaded shaft (not shown) is turned by motor 658, the threaded tongue (not shown) moves a vertical slide block 655, thereby moving the robotic head 656 along a vertical axis (e.g., the y-axis) (again, see, e.g., U.S. Pat. No. 6,467,362). The vertical slide block 655 may be directly attached to the robotic head 656, or as shown in FIG. 6, may be attached to a first rotational mechanism 664. The vertical slide block 655 has internal threads (not shown) that engage the threaded vertical shaft and operated to drive the vertical slide block, and thus the robotic head 656, in a vertical direction, along the threaded vertical shaft.

The transfer mechanism 650 may further comprise one or more rotational mechanisms operable to provide rotational movement about or around one or more axes. For example, as shown in FIG. 6, the robotic head may comprise a first rotational mechanism 664 for providing rotational movement about or around the y-axis and a second rotational mechanism 665 for providing rotational movement about or around the x-axis. The first rotational mechanism 664 comprises a first rotational plate 667 that can be attached to the robotic head 656. The first rotational mechanism 664 further comprises a first rotational motor 668, a first pinion gear 670 and a first opposable ring gear 672, which operate to rotate the first rotational plate 667, and thus the robotic head 656, about a vertical axis (e.g., about the y-axis). In one embodiment, as is well known in the art, the first pinion gear 670 and first ring gear 672 may be provided with gripping teeth (not shown) or other gripping feature (not shown). The first rotational plate 667 may be directly attached to the robotic head 656, or as shown in FIG. 6, may be attached to a second rotational mechanism 665. Also as shown in FIG. 6, the first rotational plate 667 may comprise a bent plate to facilitate attachment to the second rotational mechanism 665. The second rotational mechanism 665, like the first rotational mechanism 664, comprises a second rotational plate 674. As shown in FIG. 6, the second rotational plate 674 is attached to the robotic head 656. The second rotational mechanism 665 further comprises a second rotational motor 678, a second pinion gear 680 and a second opposable ring gear 682, which operate to rotate the second rotational plate 674, and thus the robotic head 656, about a horizontal axis (e.g., the x-axis). In one embodiment, as is well known in the art, the second pinion gear 680 and second ring gear 682 may be provided with gripping teeth (not shown) or other gripping feature (not shown).

The robotic head 656, best shown in FIG. 7B, comprises a housing 684 enclosing a holding chamber 685 for holding a single specimen container 500 therein. The robotic head further comprises a gripping mechanism 686 and a drive mechanism 688 to move the gripping mechanism 686, and thereby a single specimen container 500, into and out of the housing 684 and holding chamber 685. The gripper mechanism 686, as shown in 7B, may comprise a spring clip 687 operable to snap over the lip of a specimen container 500. After transferring the specimen container 500 to a holding structure 600, as described elsewhere herein, the robotic head 656, and thus the gripping mechanism 686, can be raised or lowered relative to the holding structure 600 to release the specimen container 500. The drive mechanism 688 further comprises a motor 690, a guide rail 692, a threaded gripper shaft 694 and a gripper drive block 696, as shown in FIG. 7B. In operation, the motor 690 turns the threaded gripping shaft 694, thereby moving the gripping drive block 696, and thus the gripping mechanism 686 along the guide rail 692.

Another design possibility of the transfer mechanism is shown in FIGS. 9A-9B. As shown in FIGS. 9A-9B an automated transfer mechanism 820 is incorporated into the detection system 100 shown in FIGS. 9A-9B in order to grasp or pick-up a container 500 from the entrance location or port 110, and move or transfer a container 500 to a give receiving structure or well 802, of an upper or lower drum holding structure 800 (described elsewhere herein). The automated transfer mechanism 820 in this embodiment is also operable to move a negative container 500 to a waste location and subsequently dropping or otherwise depositing the container 500 into a waste bin 146, or operable to move a positive container to a positive container location (see, e.g., 130 in FIG. 1). To provide such movement, the transfer mechanism 820 includes a robotic head 824 which may include a gripping mechanism 826 for picking-up and holding a container 500, and a rotatable support rod 828 that extends across the interior chamber 850 of the system 100. As shown, the robotic head 824 is supported by, coupled to, and/or attached to the rotatable support rod 828. In general, the gripping mechanism can be any known gripping mechanism in the art. In one embodiment, the gripping mechanism may be the gripping mechanism and drive mechanism described hereinabove in conjunction with FIGS. 6-8C. The robotic head 824 is moveable to any position along the rotatable support rod 828. In operation, the support rod 828 can be rotated about its longitudinal axis, so as to orient the robotic head 824 towards either the upper or lower cylinder or drum holding structures 800A, 800B.

In one embodiment, the robotic head 820 is operable to pick-up a container 500 from the entrance location or port 110 and load the container 500 head-first (i.e., top portion 502 first) into the receiving structures or wells 802 of the drum holding structures 800A, 800B. This orientation exposes the bottom or base 506 of the container 500 to a detection unit 810 which can read the sensor 514 located at the bottom of the container 500 to detect microbial or microorganism growth within the container.

Figure 20:
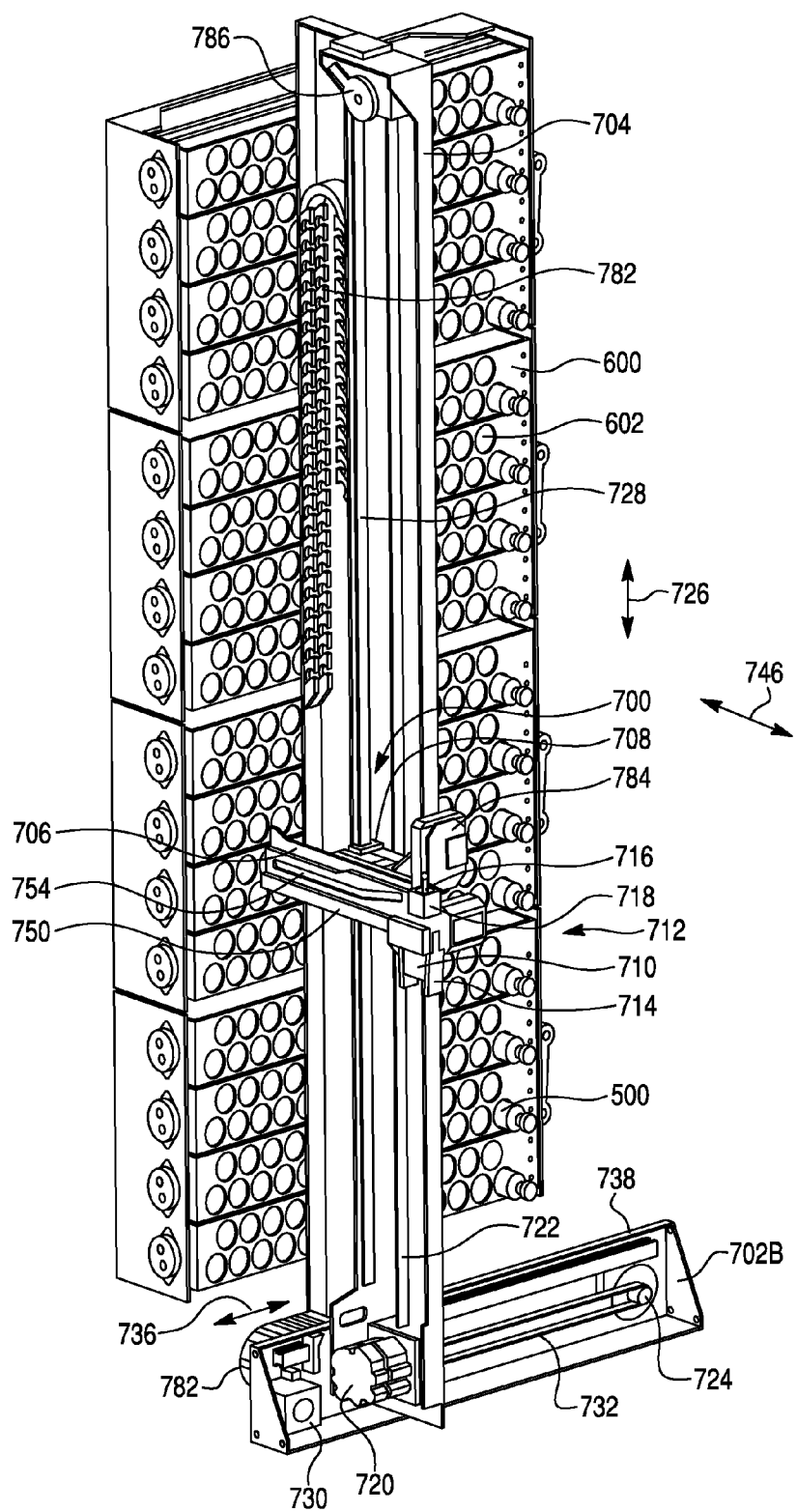
FIG. 20 is a perspective view of the holding structure and automated transfer mechanism shown in FIGS. 17-19. As shown, in this embodiment, the automated transfer mechanism comprises a lower horizontal support, a vertical support, a pivot plate and a robotic head for transferring a specimen container within a detection apparatus. For clarity, the holding structure and automated transfer mechanism are shown isolated from the detection apparatus.

Yet another design possibility for the transfer mechanism is shown in FIGS. 17-21B. As shown in FIGS. 17-21B, the robotic transfer arm 700 will include one or more horizontal support structures 702, one or more vertical support structures 704, and a robotic head 710 that will include one or more features or devices (e.g., a gripping mechanism) to pick-up, grip and/or hold a specimen container 500. The robotic head 710 can be supported by, coupled to, and/or attached to one of the horizontal supports and/or vertical supports. For example, in one embodiment, as shown in FIGS. 17-21B, the robotic transfer arm 700 comprises a lower horizontal support structure 702B and a single vertical support structure 704. Although, not shown, as one of skill in the art would appreciate an upper horizontal support structure (not shown), or other similar means can be used to further support or guide the vertical support structure. In general, any known means in the art can be used to move the robotic head 710 up and down the vertical support rail 704 (as represented by arrow 726 (see FIG. 18)), and move the vertical support rail 704 back-and-forth along the horizontal support structure(s) 702B (as represented by arrow 736 (see FIG. 20)). For example, as shown in FIG. 20, the robotic transfer arm 700 may further comprises a vertical drive motor 720 and vertical drive belt 722 that will operate to transfer or move the robotic head 710 up and down (arrow 726) the vertical support rail 704 to transfer or move a container 500 along (i.e., up and down) a vertical axis (i.e., the y-axis). The vertical support structure 704 may further comprise a vertical guide rail 728 and a robotic head support block 708, as shown in FIG. 20. Accordingly, the vertical support structure 704, vertical guide rail 728, vertical drive motor 720 and vertical drive belt 722 allow the robotic transfer arm 700 to move or transfer the robotic head support block 708, and thus, the robotic head 710 and a specimen container 500 along the y-axis. Likewise, also as shown in FIG. 20, the robotic transfer arm 700 may further comprise a first horizontal drive motor 730, first horizontal drive belt 732 and horizontal guide rail 738 that will operate to move the vertical support structure 704 back-and-forth (i.e., from left-to-right and/or from right-to-left) along the horizontal guide rail 738, and thus, along a first horizontal axis (i.e., the x-axis) within the housing 102 of the detection system 100 (see arrow 736)). Accordingly, the horizontal support structure(s) 702B, first horizontal drive motor 730, first horizontal drive belt 732 and horizontal guide rail 738 allow the robotic transfer arm 700 to move or transfer a specimen container 500 along the x-axis. Applicants have found that by including a vertical support that is movable along a horizontal axis allows for an increased capacity within the detection system, as the robotic transfer arm is movable over an increased area within the instrument. Furthermore, Applicants believe a robotic transfer arm having a movable vertical support may provide a more reliable robot transfer arm.

Figure 21A:
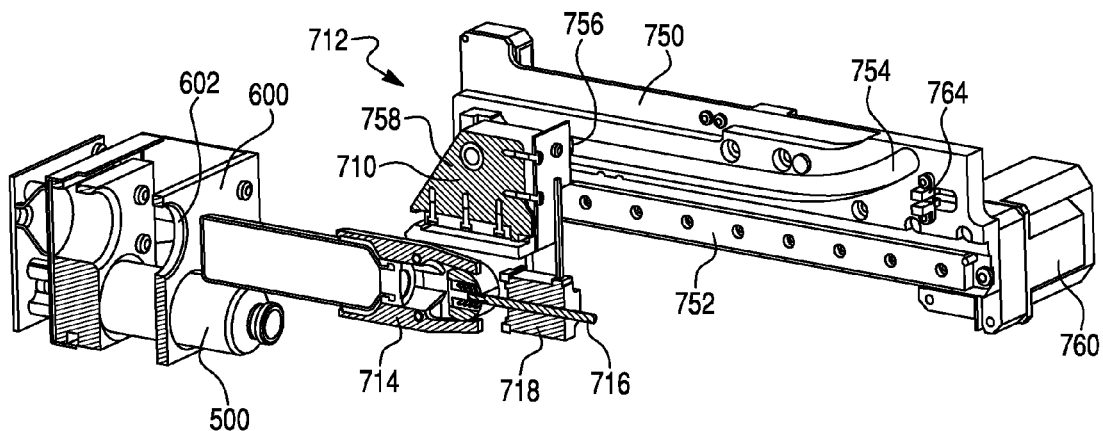
FIGS. 21A-B are perspective views of the pivot plate and robotic head of the automated transfer mechanism shown in FIG. 20. The robotic head is shown with a cross-sectional view of the gripping mechanism and specimen container to reveal the features of the gripping mechanism.
Figure 21B:
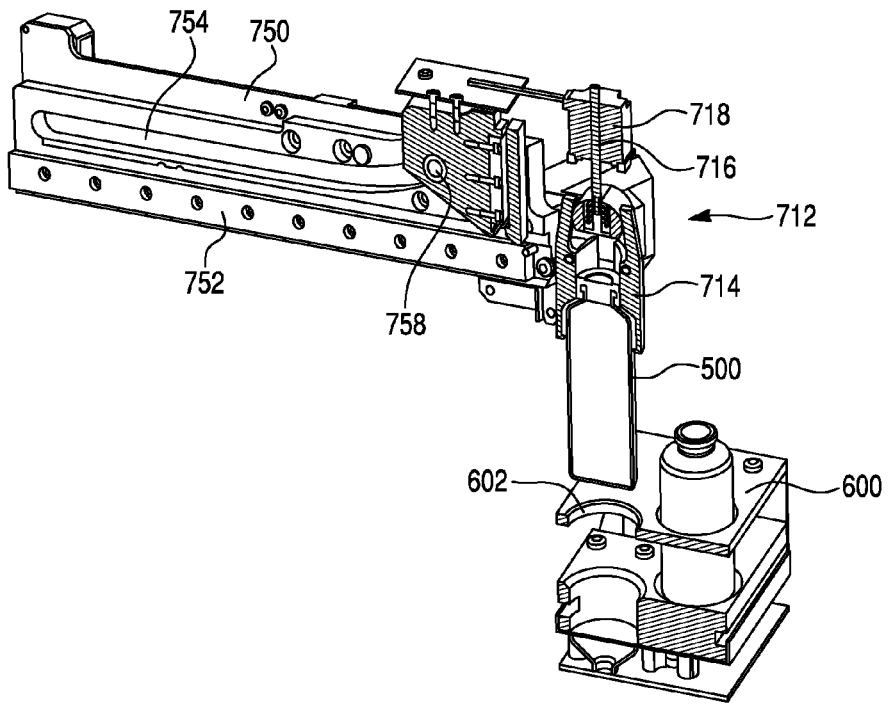

As shown best in FIG. 17-21B, the automated transfer mechanism or robotic transfer arm 700 may further comprise a linear or horizontal slide 706 and pivot plate 750. As shown, for example in FIGS. 17-20, the linear or horizontal slide 706 supports the robotic head 710 and gripper mechanism 712. The linear or horizontal slide 706 and robotic head 710 may be supported by, coupled to, and/or attached to, a robotic head support block 708 and vertical guide rail 728 (previously described). In accordance with this embodiment, the linear or horizontal slide 706 can be moved up and down (see FIG. 18, arrow 726) along a vertical axis (i.e., the y-axis), via the a robotic head support block 708 and vertical guide rail 728, to move or transfer the robotic head 710 and/or specimen container 500 up and down within the housing 102 of the detection system 100 (i.e., along the vertical axis (y-axis)). As shown in FIGS. 21A-21B, the linear or horizontal slide 706 may further comprises a pivot plate 750 comprising a pivot plate guide rail 752, a pivot slot 754 and pivot slot cam follower 756 operable to allow the robotic head 710 to slide or moved along the linear or horizontal slide 706, from front-to-back or from back-to-front (see FIG. 18, arrow 746), to transfer or move a container 500 along a second horizontal axis (i.e., the z-axis). In accordance with this embodiment, a second horizontal drive motor or horizontal slide motor 760 and a slide belt (not shown) can be used to move the robotic head 710 along the z-axis. Accordingly, the linear or horizontal slide 706, the horizontal slide motor and slide belt, allows the robotic head 710 to move or transfer a specimen container 500 along the z-axis. As known in the art, one or more sensors (see, e.g., 764 in FIG. 21A) can be used to indicate the position of the robotic head 710 on the linear or horizontal slide 706.

As shown in FIGS. 21A-21B, as the robotic head 710 is moved along the linear or horizontal slide 706, pivot plate 750 and pivot plate guide rail 752, the pivot slot 754 and pivot slot cam follower 756 rotate the pivot carriage 758 about or around a horizontal axis (i.e., the z-axis), and thus, rotates the robotic head 710 from a horizontal orientation (as shown in FIG. 21A) to a vertical orientation (as shown in FIG. 21B), or vice versa. As described elsewhere herein, the transfer of a container 500 from a vertical entry orientation to a horizontal orientation may be necessary for depositing or placing the container in a horizontally orientated receiving structure or well 602 of the holding structure or rack 600. Accordingly, the pivot plate 750, pivot slot 754 and pivot carriage 758 allow the robotic head 710 to re-orientate a specimen container 500 from a vertical orientation, as loaded (see, e.g., FIG. 18) to a horizontal orientation (as seen, e.g., in FIG. 21A), thereby allowing a specimen container 500 to be transferred from an automated loading mechanism (see, e.g., 200 in FIG. 18) to a well in a holding structure (e.g., 602 and 600 in FIG. 18). As shown in FIG. 20 the automated transfer mechanism may also comprise one or more cable management chains 782, for cable management within the detection system 100, and a circuit board 784 for controlling the robotic transfer mechanism. In yet another embodiment, the robotic transfer arm 700 may further comprise a break mechanism 786 that can operate to break the vertical drive belt 722, thereby preventing if from falling to the bottom of the instrument (e.g., due to a power outage).

The robotic transfer arm 700 may further comprise a gripping mechanism 712 to pick-up, grip or otherwise hold a specimen container 500. As shown, for example in FIGS. 21A and 21B, the gripping mechanism may comprise two or more gripping fingers 714. Furthermore, the gripping mechanism 712 may further comprise a linear actuator 716 and a linear actuator motor 718 which can operate to move the linear actuator to open and close the gripper fingers 714. In operation, as is well known in the art, the actuator motor 718 can be used to move the linear actuator 716 of the gripper mechanism 712 thereby moving the gripper fingers 714. For example, the linear actuator can be moved in a first direction (e.g., toward the motor) to close the fingers and grip the container 500. Conversely, the linear actuator can be moved in a second direction (e.g., away from the motor) to open the gripper fingers and release the container 500. Applicants have unexpectedly found that the use of one or more gripping fingers 714 allows the gripping mechanism 712 to accommodate (i.e., pick-up and/or hold) a large variety of different specimen containers 500. Moreover, Applicants have found that by using gripper fingers 714 that extend from about one-quarter (¼) to about one-half (½) the length of the specimen container 500, the gripper fingers will accommodate (i.e., pick-up and/or hold) a number of well known containers (e.g., long neck blood culture bottles) in the art.

As described further herein, the automated transfer mechanism or robotic transfer arm 700 can be placed under the control of a system controller (not shown) and programmed for specimen container 500 management (e.g., pick-up, transfer, placement and/or container removal) within the detection system 100.

In yet another embodiment, as discussed further hereinbelow, the transfer mechanism 700 can be used for automated unloading of "positive" and "negative" specimen containers 500.

Holding Means or Structure with Optional Agitation Means

The holding means or structure of the detection system 100 can take a variety of physical configurations for handling a plurality of individual specimen containers 500 so that a large number of containers (e.g., 200 or 400 containers, depending on the specific holding structures used) can be processed simultaneously. The holding means or structure can be used for storage, agitation and/or incubation of the specimen containers 500. One possible configuration is shown in FIGS. 5A-5B, and another possible configuration is shown in FIGS. 9A and 9B. These configurations are provided by way of illustration and not limitation. As one of skill in the art will appreciate, other designs are possible and contemplated.

As shown in FIGS. 5A-5B and FIGS. 17-20, one possible configuration uses a plurality of vertically stacked container holding structures or racks 600 each having a multitude of specimen container receiving structures or wells 602 each for holding individual specimen containers 500. In accordance with this embodiment, two or more vertically stacked holding structures or racks 600 can be used. For example, from about 2 to about 40, from about 2 to about 30, from about 2 to about 20, or from about 2 to about 15 vertically stacked holding structures or racks can be used. Referring to FIGS. 5A-5B and 17-20, in this configuration the detection system 100 includes a climate controlled interior chamber 620, comprising an upper interior chamber 622 and a lower interior chamber 624, and a plurality of vertically disposed holding structures or racks 600 (e.g., as shown in FIGS. 5A-5B, 15 vertically stacked holding structures or racks 600) each having a plurality of individual container receiving structures or wells 602 therein. Each individual holding structure or rack 600 can comprise two or more container receiving structures of wells 602. For example, each holding structure or rack 600 can comprise from about 2 to about 40, from about 2 to about 30, or from about 2 to about 20 receiving structures of wells 602 therein. In one embodiment, as shown in FIGS. 5A-5B, the receiving structures or wells 602 can comprise 2 rows of vertically aligned receiving structures or wells 602. In an alternative embodiment, the receiving structures or wells 602 can be staggered, thus reducing the vertical height of each individual holding structure or rack 600 (see, e.g., FIG. 20), and thereby allowing for an increased number of total holding structures or racks 600 in a given vertical distance within the incubation chamber 620. As shown, for example in FIGS. 5A-5B, the detection system comprises 15 holding structures or racks 600 each comprising two rows of 10 individual container receiving structures or wells 602, thereby giving the system exemplified in FIGS. 5A-5B a total container capacity of 300. In another possible design configuration, the detection apparatus may comprise 16 vertically stacked racks, each containing 25 receiving structures or wells, thereby giving a total container capacity of 400.

Furthermore, each of the individual container receiving structures or wells 602 has a specific X and Y coordinate position or address, where X is the horizontal location and Y is the vertical location of each container receiving structure or well 602. The individual wells 602 are accessed by a transfer mechanism, such as a robotic transfer arm, for example, as described hereinabove in conjunction with FIGS. 17-21). As shown in FIGS. 17-21, the automated transfer mechanism 700 can operate to move the robotic head 710, and thus, the specimen container 500, to a specific of the X, Y positions in the rack 600 and deposit the container 500 therein. In operation, the automated transfer mechanism 700 can operate to pick-up a specimen container 500 at the entrance station 110 or the pick-up station 418 of the container locator device 400, move a container 500 determined positive for microbial growth therein to a positive container or exit location 130, and/or to move a container 500 determined negative for microbial growth to a negative container location or waste bin 146.

In one embodiment, the entire holding structure or rack 600 can be agitated by an agitation assembly (not shown) to promote or enhance microorganism growth. The agitation assembly can be any known means or mechanism for providing agitation (e.g., a back-and-forth rocking motion) to the holding structures or racks 600. In another embodiment, the holding structures or racks 600 can be rocked in a back-and-forth motion for agitation of the fluid contained within the containers. For example, the holding structures or racks 600 can be rocked back-and-forth from a substantially vertical position to a substantially horizontal position, and repeated to provide agitation of the fluid contained within the container. In yet another embodiment, the holding structures or racks 600 can be rocked back-and-forth from a substantially horizontal position to a vertical position 10 degrees, 15 degrees, 30 degrees, 45 degrees or 60 degrees from horizontal, and repeated to provide fluid agitation within the containers. In one embodiment, a racking motion from a substantially horizontal position to a vertical position from about 10 degrees to about 15 degrees from horizontal may be preferred. In still another embodiment, the holding structure or racks 600 can be rocked back-and-forth in a linear or horizontal motion to provide agitation of the fluid contained within the containers. In this embodiment, the holding structures or racks 600 and receiving structures or wells 602 can be orientated in a vertical, or alternatively in a horizontal position. Applicants have found that a linear or horizontal agitation motion, with the holding structures 600, and thus the receiving structures or wells 602 and specimen containers 500, in a horizontal orientation can provide substantial agitation with a relatively minimum energy input. Accordingly, in some embodiments, a horizontal holding structure or rack 600 orientation and a linear or horizontal agitation motion, may be preferred. Other means of agitating the holding structures or racks 600, and thus, the fluid within specimen containers 500 are contemplated and would be well understood by one skilled in the art. These back-and-forth, liner and/or horizontal rocking motions can be repeated as desired (e.g., at various cycles and/or speeds) to provide agitation of the fluid within the containers.

One possible design for the agitation assembly is shown in conjunction with FIG. 26. As shown in FIG. 26, the agitation assembly 626 comprises one or more holding structures 600 comprising a plurality of holding wells 602 for holding a plurality of specimen containers 500. The agitation assembly 626 further comprises an agitation motor 628, an eccentric coupling 630, a first rotation arm 632, a second rotation arm or linkage arm 634 and a rack agitation bearing assembly 636. In operation, the agitation motor 628 rotates the eccentric coupling 630 in an off-center motion thereby moving a first rotation arm 632 in an off-center circular or off-center rotational motion. The off-center rotational movement of the first rotation arm 632 moves a second rotation arm or linkage arm 634 in a linear motion (as represented by arrow 635). The linear motion of the second rotation arm or linkage arm 634 rocks the rack agitation bearing assembly 636 in a back-and-forth rocking motion, thereby providing a back-and-forth rocking agitation motion (represented by arrow 638 of FIG. 26) to the holding structures 600.

In another possible design configuration, as shown in FIGS. 9A and 9B, the detection system 100 may includes upper and lower holding structures 800A and 800B in the form of cylindrical or drum structures containing a multitude of individual specimen container receiving structures or wells 802 for receiving one of the containers 500. In this embodiment, the cylindrical or drum holding structures 800A, 800B each rotate about a horizontal axis to thereby provide agitation of the containers 500. In accordance with this embodiment, each drum holding structure can comprise from about 8 to about 20 rows (e.g., from about 8 to about 20, from about 8 to about 18, or from about 10 to 1 about 6 rows), each comprising from about 8 to about 20 container receiving structures or wells 802 (e.g., from about 8 to about 20, from about 8 to about 18, or from about 10 to about 16 receiving structures of wells 802).

As described hereinabove, an automated transfer mechanism 820 is incorporated into the detection system 100 of FIGS. 9A-9B in order to grasp or pick-up a container 500 from the entrance location or port 110, and move or transfer the container 500 to a give receiving structure or well 802, of either the upper or lower drum holding structure 800, and deposit the container 500 therein. The automated transfer mechanism 820 in this embodiment can further operate to move a negative container 500 to a waste bin 146, or can operate to move a positive container to the positive container location 130, shown for example, in FIG. 1. Also, as previously described, the robotic head 820 of FIGS. 9A-9B can pick-up a container 500 from the entrance location or port 110 and load the container 500 head-first (i.e., top portion 502 first) into the receiving structures or wells 802 of the drum holding structures 800A, 800B. This orientation exposes the bottom or base 806 of the container 500 to a detection unit 810 which can read the sensor 514 located at the bottom of the container 500 to detect microbial or microorganism growth within the container.

As described elsewhere herein, positive and negative containers can be retrieved by the robotic transfer arm and transferred to other locations within the system. For example, a container determined "positive" for microbial growth can be retrieved and transferred via the transfer mechanism to a positive container location or port where a user or technician can easily remove the positive container. Similarly, a container determined "negative" for microbial growth after a designated time has passed can be transferred via the transfer mechanism to a negative container location or waste bin for disposal.

Figure 27A:
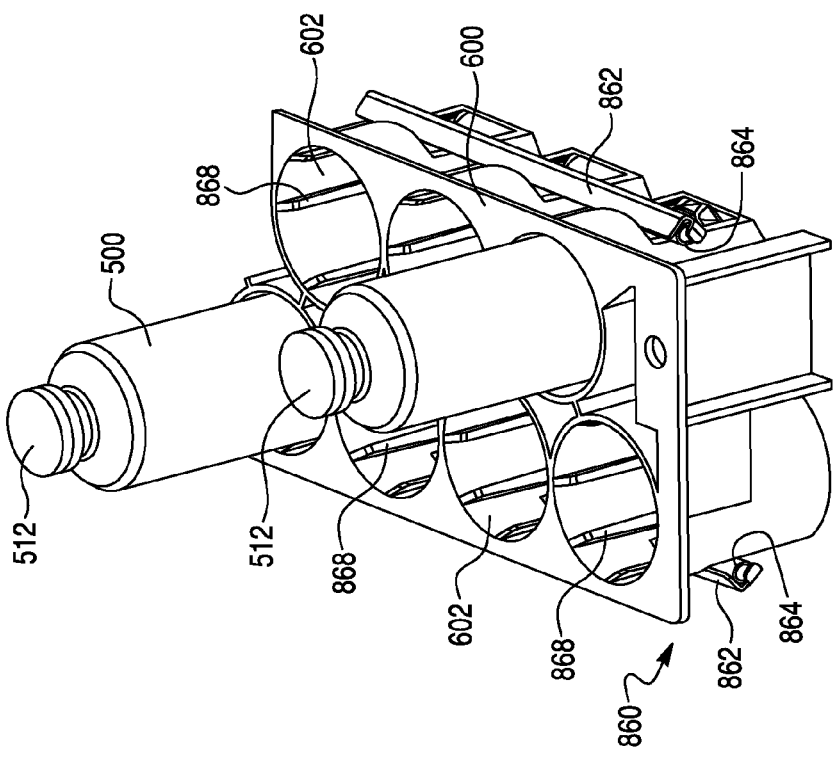
FIG. 27A is a perspective view of a rack holding structure and retention feature for holding a specimen container securely within the rack holding structure.
Figure 27C:
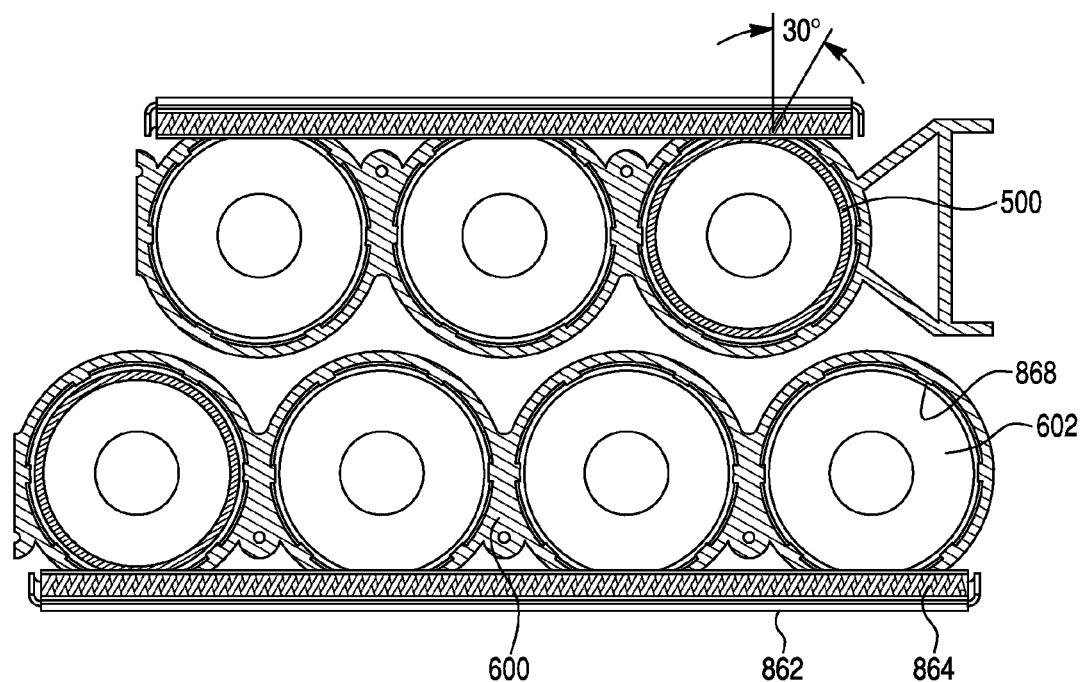
FIG. 27C is a top cross-sectional view of the rack holding structure and retention feature of FIG. 27A, showing a schematic representation of a canted coiled spring.

In one embodiment, the holding structure or rack 600 may further comprise a retention feature operable to hold or otherwise retain a specimen container 500 in the receiving structures or wells 602 of the rack 600. As shown in FIGS. 27A-27C, the retention device 860 comprises a canted coiled spring 864 and a v-shaped holding plate 862. In accordance with this embodiment, by using a canted coiled spring 868, multiple points of the coiled spring contact the container surface to retain the bottle in the rack well 602. The coils of the canted spring 864 are set at an angle relative to the vertical axis of the container, as shown in FIG. 27C, which shows exaggerated coils to demonstrate the coil angle relative to the vertical axis of the container. However, typically the canted spring 864 is a tightly coiled spring. For example the canted spring 864 can be at an angel of about 10 degrees to about 50 degrees, from about 20 degrees to about 40 degrees, or about 30 degree (as shown in FIG. 27C), relative to the vertical axis of the container. The v-shaped holding plate 862 is capable of holding and/or retaining said canted coiled spring 864 relative to, or adjacent to the holding structure 600. As shown, the holding plate 862 comprising a v-grooved retainer plate for retaining the canted coiled spring 864. The v-groove retainer plate 864 prevents any movement of the spring 864 relative to the container 500 and/or holding structure 600. Accordingly, unlike a traditional extension spring, which would typically contact a container at a single point (e.g., a flat leaf spring), the canted coiled spring 864 can be rigidly retained by the v-shaped groove 862 while the coils will deflect under pressure. The use of a canted spring 864 allows the load to be spread out, thereby providing uniform deflection.

As shown, e.g., in FIGS. 27A and 27C, the receiving structures or wells 602 further comprise one or more ribs 868. In one design possibility, as shown in FIG. 27C, two of these ribs 868 are located directly opposite the canted coiled spring 864. These two ribs 868 form a groove that functions to self-center the container 500 within the well 602 along a vertical centerline (not shown). In operation, the canted coiled spring 864 applies force to the container 500 wall, thereby holding or retaining the container securely within the well 602 of the rack 600. In one embodiment, the two ribs 868 located opposite the coiled spring 864 can be spaced from 30 degrees to about 90 degrees apart, or from about 40 degrees to about 80 degrees apart. In another embodiment, the two ribs 868 located opposite the canted coiled spring 864 can be spaced about 60 degrees apart. Also, as shown in FIG. 27C, the holding structure may comprise a first row and a second row of parallel holding wells, the parallel holding rows being capable of, or operable for, holding a plurality of containers therein, and wherein the holding structure further comprises a first canted coiled spring located adjacent to the first row and a second canted coiled spring adjacent to the second row, wherein each of the canted coiled spring are operable for retaining the plurality of containers in said holding wells.

Using the canted coiled spring 864, v-groove retainer 862 and two ribs 868 located opposite said canted coiled spring 864, the bottle will always be held securely in the same location within the well 602, regardless of any sideloads applied through agitation or during rack cell insertion. The canted coiled spring 864 and v-groove retainer 862 also allow for the use of a shorter depth holding well 602 and holding structure 600. The shorter holding well 602 depth will allow for multiple container designs and container lengths to be retained equally well, as well as allow more of the container surface to be expose to the incubation air flow within the system.

As one of skill in the art would appreciate other possible designs or configurations for the holding structure or structures 600 and/or agitation assembly are possible and are considered part of present invention.

Detection Unit

The various possible design configurations of the detection system 100, as shown in FIGS. 1-6, 9A-9B, 21A-21B and 27, can include the use of similar detection means. In general, any known means in the art for monitoring and/or interrogating a specimen container for the detection of microbial growth can be used. As previously mentioned, the specimen containers 500 can be monitored continuously, or periodically, during incubation of the containers 500 in the detection system 100, for the positive detection of microbial growth. For example, in one embodiment, a detection unit (e.g., 810 of FIG. 9B) reads the sensor 514 incorporated into the bottom or base 506 of the container 500. A variety of sensor technologies are available in the art and may suitable. In one possible embodiment, the detection unit takes colorimetric measurements as described in the U.S. Pat. Nos. 4,945,060; 5,094,955; 5,162,229; 5,164,796; 5,217,876; 5,795,773; and 5,856,175, which are incorporated herein. A positive container is indicated depending upon these colorimetric measurements, as explained in these patents. Alternatively, detection could also be accomplished using intrinsic fluorescence of the microorganism, and/or detection of changes in the optical scattering of the media (as disclosed, for example, in co-pending U.S. patent application Ser. No. 12/460,607, filed Jul. 22, 2009 and entitled, "Method and System for Detection and/or Characterization of a Biological Particle in a Sample."). In yet another embodiment, detection can be accomplished by detecting or sensing the generation of volatile organic compounds in the media or headspace of the container. Various design configurations for the detection unit can be employed within the detection system. For example, one detection unit could be provided for an entire rack or tray, or multiple detection units could be provided per rack or per tray.

Climate-Controlled Interior Chamber

As previously described, the detection system 100 may include a climate-controlled interior chamber (or incubation chamber), for maintaining an environment to promote and/or enhance growth of any microbial agents (e.g., microorganisms) that may be present in the specimen container 500. In accordance with this embodiment, the detection system 100 may include a heating element or hot air blower to maintain a constant temperature within said interior chamber. For example, in one embodiment, the heating element or hot air blower will provide and/or maintain the interior chamber at an elevated temperature (i.e., a temperature elevated above room temperature). In another embodiment, the detection system 100 may include a cooling element or cold air blower (not shown) to maintain the interior chamber at a temperature below room temperature. In accordance with this embodiment, the interior chamber or incubation chamber will be at a temperature of from about 18° to about 45° C. In one embodiment, the interior chamber can be an incubation chamber and can be maintained at a temperature from about 35° C. to about 40° C., and preferably at about 37° C. In another embodiment, the interior chamber may be maintained at a temperature below room temperature, for example from about 18° C. to about 25° C., and preferably at about 22.5° C. A particular advantage provided is the ability to provide a more constant temperature environment for promoting and/or enhancing microbial growth within a specimen container 500. The detection system 100 accomplishes this by providing a closed system, in which automated loading, transfer and unloading of specimen containers 500 occurs without the need to open any access panels that would otherwise disrupt the incubation temperature (from about 30° to 40° C., preferably from about 37° C.) of the interior chamber 620.

In general, the detection system 100 can employ any known means in the art for maintaining a climate-controlled chamber for promoting or enhancing microbial growth. For example, to maintain a temperature controlled chamber, one or more heating element or hot air blower, baffles and/or other suitable equipment known in the art, can be used to maintain the interior of the detection system 100 at the appropriate temperature for incubating the container and promoting and/or enhancing microbial growth.

Typically, one or more heating element or hot air blower under control of the system controller are used to maintain a constant temperature within the interior chamber 620 of the detection system 100. As known in the art, the heating element or hot air blower can be employed in a number of locations within the interior chamber. For example, as shown in FIGS. 5 and 6 one or more heating elements or hot air blowers 740 can be positioned at the base of the holding structures or racks 600, for directing warm air across the plurality of holding structures or racks 600. A similar arrangement can be provided in the embodiments of FIGS. 9A and 9B (see, e.g., 840). The details of the incubation features are not particularly pertinent, and are known in the art, therefore a detailed description is omitted.

Controller and User Interface

The detection system 100 will include a system controller (e.g., a computer control system) (not shown) and firmware for controlling the various operations and mechanisms of the system. Typically, the system controller and firmware for controlling the operation of the various mechanisms of the system can be any known conventional controller and firmware known to those of skill in the art. In one embodiment, the controller and firmware will performs all operations necessary for controlling the various mechanisms of the system, including: automated loading, automated transfer, automated detection and/or automated unloading of specimen containers within the system. The controller and firmware will also provide for identification and tracking of specimen containers within the system.

The detection system 100 may also include a user interface 150 and associated computer control system for operating the loading mechanism, transfer mechanism, racks, agitation equipment, incubation apparatus, and receiving measurements from the detection units. These details are not particularly important and can vary widely. When a container is detected as being positive, the user can be alerted via the user interface 150 and/or by the positive indicator 190 (see, e.g., FIG. 1) becoming active (i.e., an indicator light turning on). As described herein, upon a positive determination, the positive container can be automatically moved to a positive container location 130, shown for example in FIGS. 1-3, 10-11 and 22-24 for retrieval by a user.

Figure 22:
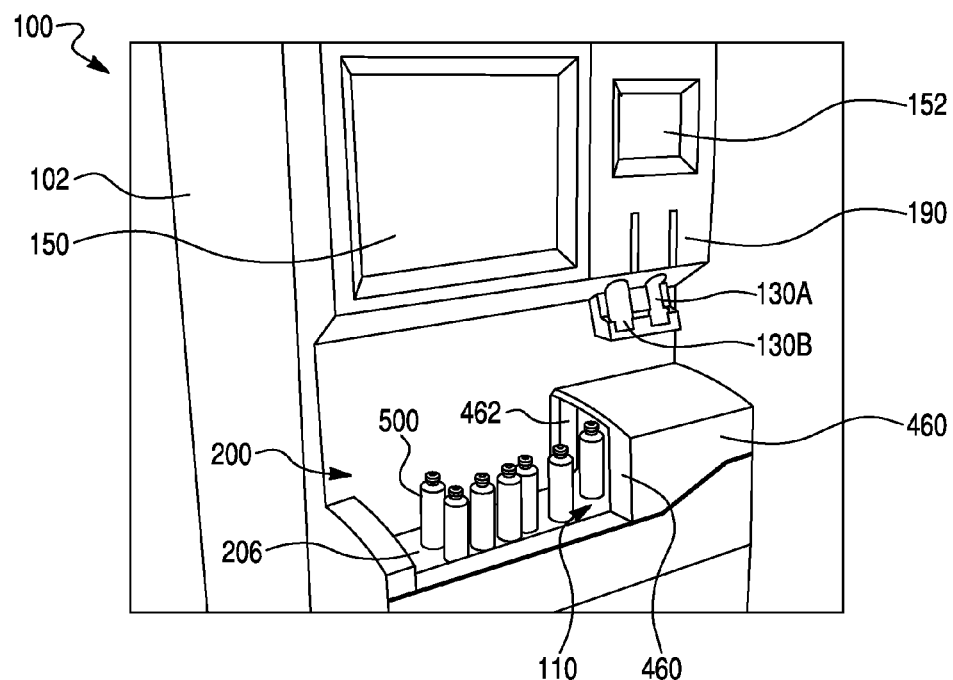
FIG. 22 is a perspective view of an alternative configuration of the automated detection apparatus showing a user interface, a status screen, a locator device cover and two positive container ports.
Figure 23:
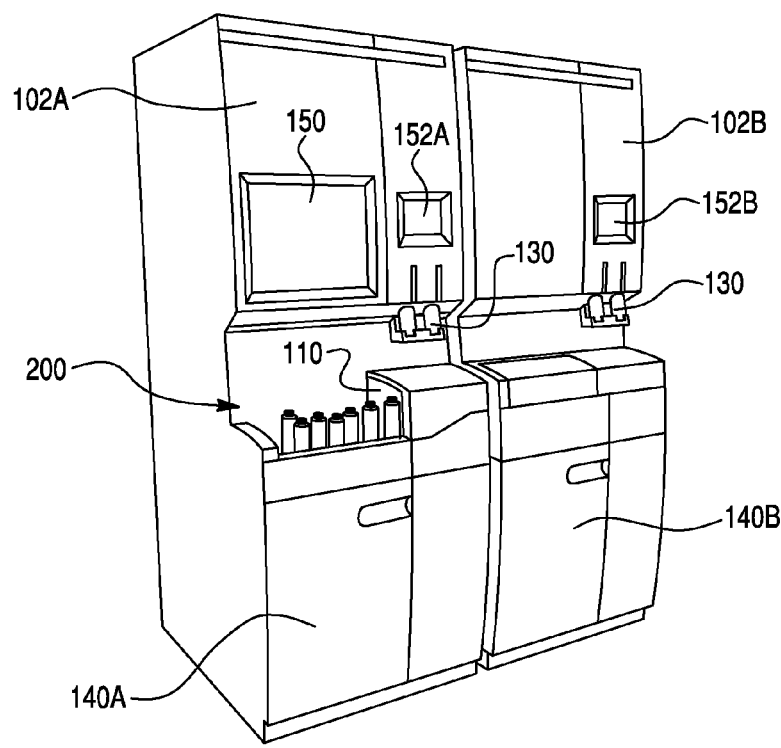
FIG. 23 is a perspective view showing another design configuration of the detection apparatus.

The user interface 150 may also provide an operator or laboratory technician with status information regarding containers loaded into the detection system. The user interface may includes one or more of the following features: (1) Touch screen display; (2) Keyboard on touch screen; (3) System status; (4) Positives alert; (5) Communications to other systems (DMS, LIS, BCES & other detection or identification Instruments); (6) Container or bottle status; (7) Retrieve containers or bottles; (8) Visual and audible Positive Indicator; (9) USB access (back ups and external system access); and (10) Remote Notification of Positives, System Status and Error Messages. In another embodiment, as shown in FIGS. 22-23, a status update screen 152 can also be used. The status update screen 152 can be used to provide status information regarding containers loaded into the detection system, such as, for example: (1) container location within the system; (2) container information, such as, patient information, sample type, input time, etc.; (3) positive or negative container alerts; (4) interior chamber temperature; and (5) an indication that the waste bin is full and needs to be emptied.

The particular appearance or layout of the detection system and user interface 150, and/or status update screen 152, is not particularly important, and can vary widely. FIGS. 1-2 show one possible embodiment, which is provided by way of illustration and not limitation. FIGS. 22-23 show another possible embodiment, which is also provided by way of illustration and not limitation.

Automated Unloading

The detection system 100 may also provide for automated transfer or automated unloading of "positive" and "negative" specimen containers 500. As previously described, containers in which a microbial agent is present are termed "positive" containers, and containers in which no microorganism growth is detected after a given time period are termed "negative" containers.

Once a container is detected as positive, the detection system will notify the operator of the results through an indicator (e.g. visual prompt 190) and/or through notification at the user interface 150. Referring now to FIGS. 1-3 and 5A-5B, positive bottles can be automatically retrieved via the transfer mechanism 650 (e.g., robotic transfer arm) and placed in a designated positive container area, such as a positive container location or exit port 130. This positive container area will be located outside of the instrument housing for easy user access to the container. In a one embodiment, the container will be placed in a vertical orientation within the positive container area. In one design configuration, the automated unloading of a positive container will employ the use of a transfer tube (not shown) through which a positive container (e.g., a positive blood culture bottle) can travel to be relocated to a designated positive container location or exit port 130. In accordance with this design feature, the transfer mechanism (e.g., the robotic transfer arm) will drop or otherwise deposit the positive specimen container into a top end of the transfer tube, and the container will travel through the transfer tube via gravity to the positive container location or port 130. In one embodiment, the transfer tube (not shown) can hold one or more "positive" specimen containers therein. For example, the transfer tube (not shown) can hold from about 1 to about 5, from about 1 to about 4, or from about 1 to about 3 "positive" specimen containers. In another embodiment, for example as shown in FIGS. 22-24, the positive container location or exit port 130 may comprise holding wells for one or more "positive" specimen containers, for example, two holding wells for separately holding two "positive" specimen containers.

In another embodiment of the detection system 100, negative containers can be transferred by the transfer mechanism 700 (e.g., robotic transfer arm) from the holding structure or rack 600 to a negative container location, such as a waste bin 146. Typically, the containers will be released from the robotic transfer arm and dropped into the waste bin 146, however other embodiments are contemplated and should be apparent to one of skill in the art. In one design configuration, the automated unloading of a negative container will employ the use of a transfer tube (not shown) through which a negative container (e.g., a negative blood culture bottle) can travel to be relocated to a designated negative container location, such as a waste bin 146. In accordance with this design feature, the transfer mechanism (e.g., the robotic transfer arm) will drop or otherwise deposit the negative specimen container into a top end of the transfer tube, and the container will travel through the transfer tube via gravity to the negative container location or waste bin 146. The detection system 100 may also include an access door 140 or drawer 142 that opens to provide user access to the negative container location, such as a negative container waste bin 146. In another embodiment, the waste bin 146 may include a scale to weigh the waste bin 146. As one of skill in the art would appreciate, by monitoring the weight of the waste bin 146, the system controller (not shown) can determine how full the waste bin 146 is, and can optionally provide a signal (e.g., at the user interface 150) indicating to the user or technician that the waste bin 146 is full, and thus, needs to be emptied.

Automated Laboratory System

As noted above, the detection system 100 of this disclosure can take on a variety of different possible configurations. One such configuration, particularly suited for high volume implementations, is shown in FIG. 24. As shown in FIG. 24, the detection system 100A can be employed in an automated microbiology laboratory system. For example, the detection instrument 100 can be included as one component of an automated laboratory system. In this embodiment, the detection instrument 100A can be linked or "daisy chained" to one or more additional other analytical modules or instruments for additional testing. For example, as shown in FIG. 24, the detection instrument 100A can be linked or "daisy chained" to a second detection unit 100B. However, in other embodiments, the detection instrument can be "daisy chained" or otherwise linked to one or more other systems or modules. These other systems or modules can include, for example, identification testing systems such as the VITEK or VIDAS systems of the assignee bioMérieux, Inc., a gram stainer, a mass spectrometry unit, a molecular diagnostic test system, a plate streaker, an automated characterization and/or identification system (as disclosed in co-pending U.S. patent application No. 60/216,339, entitled "System for Rapid Non-invasive Detection of a Microbial Agent in a Biological Sample and Identifying and/or Characterizing the Microbial Agent", which was filed May 15, 2009) or other analytical systems.

Referring now to FIG. 24, an automated laboratory system can comprise a first detection system 100A, and a second detection system 100B. In other embodiments, the automated laboratory system can comprise a first detection system 100A, a second detection system 100B, and an automated characterization/identification system (not shown). In accordance with this embodiment, positive containers can be moved or transferred from the first detection system 100A to the second detection system 100B, and/or subsequently to the automated characterization/identification system, using a system transfer device 440. In other embodiments, the first detection system 100A can be coupled to a microorganism identification module or an antimicrobial susceptibility module (not shown).

Figure 25A:
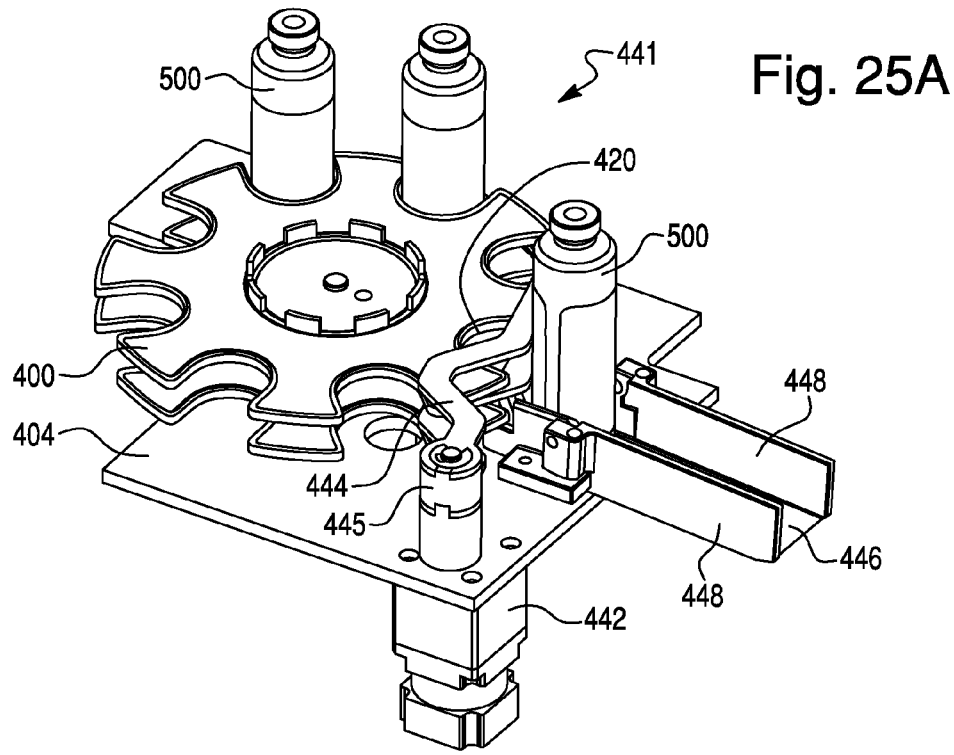
Figure 25B:
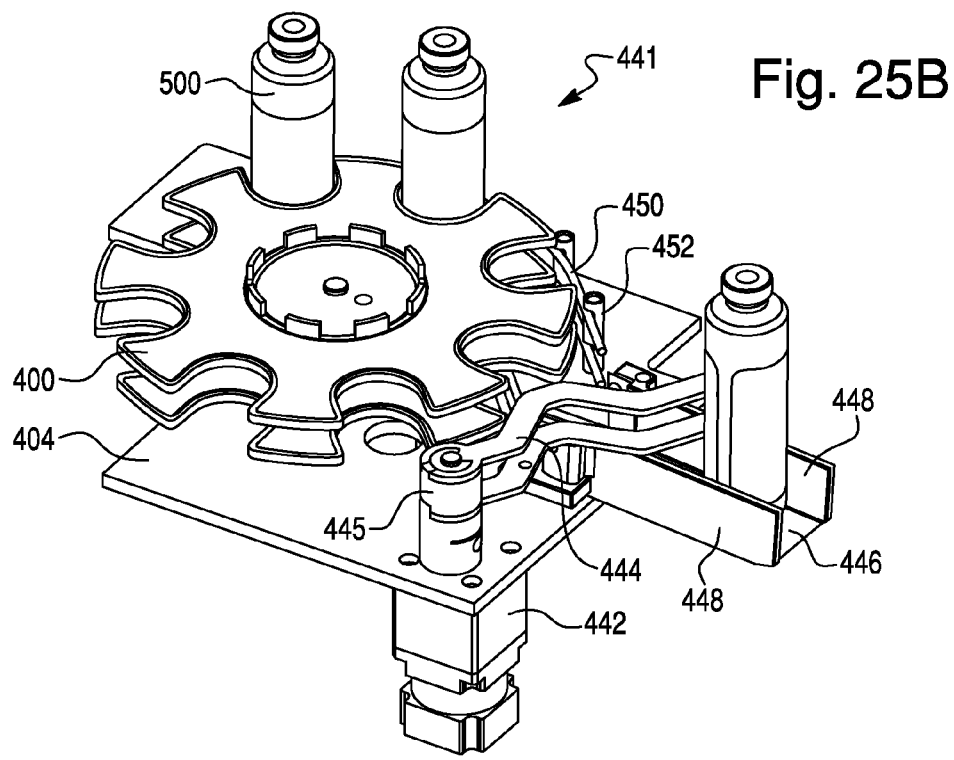

As shown in FIGS. 24-25C two detection systems 100A and 100B are "daisy chained" together by system transfer device 441. This allows containers to be transferred from one detection system to another in case the first one is full. A similar system transfer device may also be provided for subsequent transfer of the specimen container 500 from the second detection system 100B to a subsequent systems or modules, as described elsewhere herein. The system transfer mechanism 441 comprises a first container locator device 400A having a transfer station 420 for transferring a container to a second or downstream instrument. The system transfer mechanism 441 also comprises a pusher arm 444 operable controlled by a pusher motor 442 and a transfer bridge 446, as shown in FIG. 24-25C. As shown, the pusher arm 444 may comprise a pair of parallel arms. In operation, when a container to be transferred is moved by the transfer station 420 of the first container locator device 400A, a pusher arm 444 is activated to push or move the container from the transfer station 420, across a transfer bridge 446, to the down-stream detection system 100B. As shown, the pusher arm 444 is connected to a pusher motor 442 via a pusher arm support structure 445. FIGS. 25A-C show the transfer of a container from the transfer station 420 of the first detection system 100A to the conveyor belt 206B (see FIG. 24) of the second detection system 100B, and show the container in: (1) a first position (FIG. 25A) as the pusher arm 444 begins to push the container across the transfer bridge 446; (2) a second or intermediate position (FIG. 25B) as the container crosses the transfer bridge 446; and (3) a final position (FIG. 25C) as the container arrives at the conveyor belt (not shown) of the down-stream detection system 100B. Furthermore, as shown in FIGS. 25A-25C, the system transfer device 440 may further comprise one or more locator device guide rails 450 attached to a base plate of the locator device 404 via one or more guide rail supports 452, and/or bridge guide rails 446, 448, to guide the container from the first locator device 400A and across the bridge 446 to the conveyor belt 206B (see FIG. 24) of the automated loading mechanism 200B of the down-stream detection system 100B. As would be well known in the art, the transfer of a container from the first detection system 100A to the second or down-stream detection system 100B, via the operation of the first container locator device 400A and pusher arm 444, can be controlled by the system controller. Typically, as shown in FIG. 24, only the first detection system 100A needs to include a user interface 150. The first 100A and second 100B detection systems may further comprise status screens 152A, 152B, positive container ports 130A, 130B, lower access panels 140A, 140B, automated loading mechanisms 200A, 200B and conveyor belts 206A, 206B.

Further, in accordance with this embodiment, positive containers can be transferred to other systems in the automated laboratory system. For example, as shown in FIG. 24, a container determined positive in the first detection system 100A can be transferred to the second detection system 100B and/or subsequently to an automated characterization/identification system (not shown) for automated characterization and/or identification of the microbe therein.

As one of skill in the art would appreciate other possible designs or configurations for the automated laboratory system are possible and are considered part of this invention.

Method of Operation

In one embodiment, a method for detection of microorganism growth in an automated detection system is described herein; the method comprising: (a) providing a specimen container comprising a culture medium for promoting and/or enhancing growth of said microorganism; (b) inoculating said specimen container with a test sample to be tested for the presence of a microorganism; (c) loading said inoculated specimen container into said detection system using an automated loading mechanism; (d) transferring said specimen container to a holding structure located within said detection system using an automated transfer mechanism, said holding structure comprising a plurality of wells for holding one or more of said specimen containers; and said holding structure optionally providing agitation of said specimen containers to promote and/or enhance microorganism growth therein; (e) providing a detection unit for detecting microbial growth in said specimen container by detecting one or more by products of microorganism growth within said container; and (f) detecting growth of a microorganism using said detection unit and thereby determining said container positive for microorganism growth.

Figure 30:
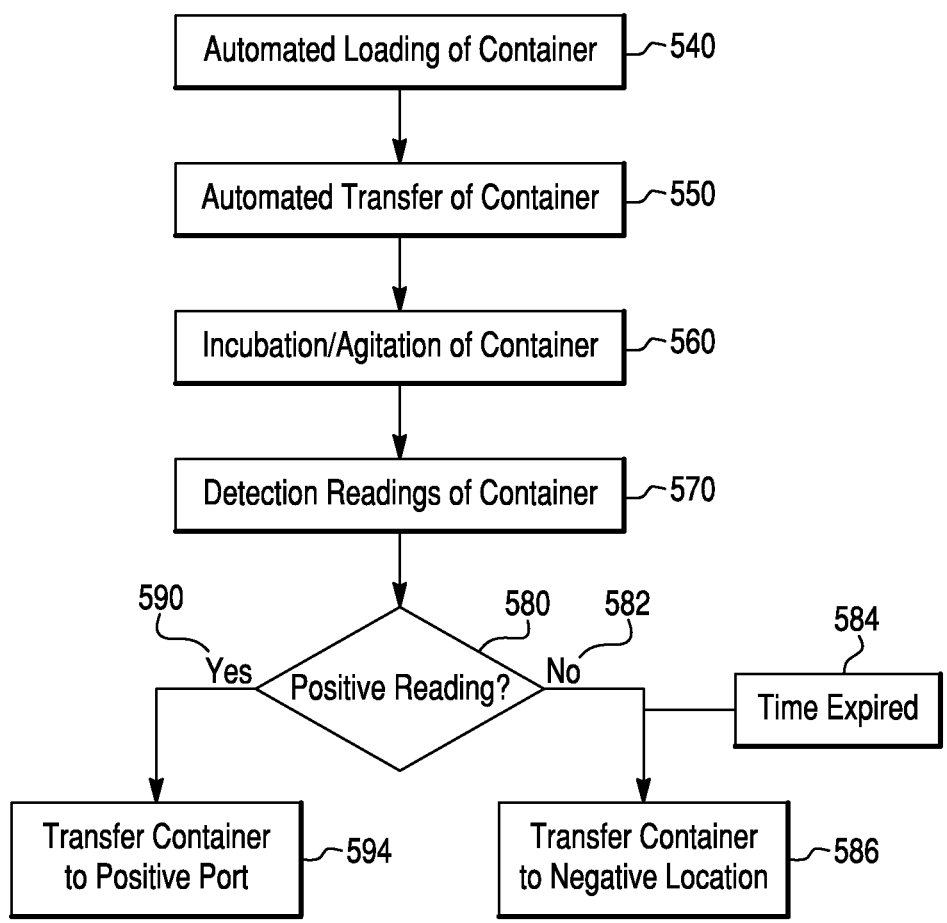
FIG. 30 is a flow chart showing the steps performed in the operation of the detection system.

The method of operation of the detection system 100 will now be described with reference to FIG. 30. After inoculation of a specimen container 500 with a sample to be tested (e.g., by a laboratory technician or doctor) the specimen container 500 is delivered to the automated loading mechanism 200, for automated loading of the specimen container 500 into the detection system 100.

At step 540, the specimen container 500 is loaded into the detection system 100, e.g., by placing the container onto a loading station or area 202 of a transport mechanism 204, as shown for example in FIG. 1. The specimen container 500 is then moved by the transport mechanism 204 (e.g., a conveyor belt) to an entrance location or port 110, and subsequently through said entrance location or port 110 and into the detection system 100, thereby automatically loading the specimen container 500 into the detection system 100.

At step 550, an automated transfer mechanism 700, such as a robotic transfer arm, as shown for example in FIGS. 5A-5B, can then be used to transfer the container 500 to, and deposit the container in, a holding structure or rack 600 contained within the interior chamber 620 of the detection system 100.

At step 560, the specimen container 500 is incubated within the detection system 100. The detection system 100 optionally provides for agitation (e.g., using an agitation assembly) of the holding structures or racks 600, and/or one or more warm air blowers (see, e.g., 740 in FIGS. 5A-5B) to provide a temperature controlled environment, to promote and/or enhance microbial growth within the specimen container 500.

At step 570, the specimen container 500 is read by a detection unit (see, e.g., 810 in FIGS. 9A and 9B) to determine if the specimen container 500 is positive for microbial growth.

At step 580, the reading of the specimen container is analyzed to determine if the container is positive for the growth of a microbial agent (e.g., a microorganism) therein. If not, the processing proceeds along the NO branch 582 and a check is made if a timer has expired (step 584). If the timer has expired, the container is deemed negative and the container is transferred to the waste container 146 (see for example FIG. 1) at step 586. Otherwise, the incubation continues and the reading of the specimen container 500 (step-580) continues periodically.

If at step 580, if the specimen container 500 is determined to be positive, the processing proceeds to the YES branch 590. In one embodiment, the specimen container 500 is moved or transferred using the automated transfer mechanism (e.g., the container is automatically unloading, as described elsewhere herein) to the positive container location or port 130 (see for example FIG. 1) at step 594 for user access to the container and/or further processing. In another embodiment, the specimen container can be transferred using a system transfer device to another detection instrument and/or another analytical system (e.g., to an automated characterization and/or identification system) for further processing.

That which is claimed is:

1. An automated detection apparatus for rapid non-invasive detection of microorganism growth in a test sample, comprising: a housing enclosing an interior chamber;
a holding structure having a plurality of wells for holding one or more specimen containers, wherein the holding structure further comprises a retention feature operable to hold the specimen container in one of the plurality of wells, the retention feature comprising a canted coiled spring and a v-shaped holding plate, and wherein said holding structure further comprises an agitation assembly;
a detection unit located within said interior chamber for the detection of microorganism growth in the specimen container;
an automated loading mechanism for automated loading of said specimen container into said interior chamber, wherein said automated loading mechanism comprises a first end and a second end, said automated loading mechanism further comprising a container loading station located at said first end, a conveyor belt, one or more guide rails, and a container entrance location located at said second end, and wherein said conveyor belt is configured to transport said specimen container from said loading station to said container entrance location, and subsequently through said container entrance location, wherein said one or more guide rails guide the specimen container into a single file line at the second end of the automated loading mechanism;
a container locator device located within said housing, said container locator device comprising a rotatable disk containing one or more locator wells each capable of holding a single specimen container and a pusher arm attached to a pusher motor via a pusher support structure, said rotatable disk configured to rotate in a horizontal plane about a vertical axis and thereby locate said specimen containers among a plurality of workflow stations comprising a container imaging station, a container pick-up station, and a container transfer station , wherein the pusher arm rotates around a vertical axis through the pusher support structure to advance the single specimen container to a downstream instrument when the single specimen container reaches the container transfer station; and wherein said conveyor belt is configured to place one of said specimen containers into one of said locator wells.

2. The automated detection apparatus of claim 1, wherein said detection apparatus further comprises an automated transfer mechanism located within said interior chamber configured for the automated transfer of said specimen container from said container transfer station to within said interior chamber.

3. The automated detection apparatus of claim 2, wherein said automated transfer mechanism comprises a robotic transfer arm, said robotic transfer arm comprising a multi-axis robotic transfer arm.

4. The automated detection apparatus of claim 1, wherein said interior chamber comprises an incubation chamber, said incubation chamber comprising one or more heating elements to provide and/or maintain a climate-controlled interior chamber.

5. The automated detection apparatus of claim 1, wherein said first transport mechanism further comprises a backing board located underneath said conveyor belt.

6. The automated detection apparatus of claim 1, wherein said automated loading mechanism further comprises a second transport mechanism for transporting said specimen container from said first transport mechanism to said container entrance location.

7. The automated detection apparatus of claim 6, wherein said second transport mechanism comprises a second conveyor belt, and wherein said second conveyor belt is located in a vertical plane above said first conveyor belt and operable in said vertical plane to provide said specimen container with clockwise or counter-clockwise rotation, thereby preventing two or more of said specimen containers from becoming trapped or jammed at said entrance location.

8. The automated detection apparatus of claim 6, wherein said second transport mechanism comprises a second conveyor belt, and wherein said second conveyor belt further comprises a plurality of paddles.

9. The automated detection apparatus of claim 1, wherein said apparatus further comprises a controller for operating said automated loading means.

10. The automated detection apparatus of claim 1, wherein said container entrance location comprises a rotating turntable for rotating the container within the entrance location to enable reading of a bar code label.

11. The automated detection apparatus of claim 3, wherein the robotic transfer arm further comprises:
a horizontal slide supporting a robotic head and a gripper mechanism; and
a pivot plate comprising a pivot plate guide rail, a pivot slot, and a pivot slot cam follower operable to allow the robotic head to slide along the horizontal slide,
wherein the gripper mechanism is configured to pick up the specimen container at the container pick-up station,
wherein the robotic head rotates from a vertical orientation to a horizontal orientation as the robotic head slides along the horizontal slide, and
wherein the specimen container is transferred to one of the plurality of wells in the holding structure in the horizontal orientation.

12. A method for the automated loading of a specimen container into a detection system, the method comprising:
providing a specimen container;
providing said detection apparatus as claimed in claim 1, wherein said automated loading mechanism further comprises;
a loading station located on said housing for receiving one or more of said specimen containers, and
an entrance location in said housing, said entrance location comprising an opening in said housing for transport of a specimen container therethrough;
depositing said specimen containers on said loading station; and
transporting said one or more specimen containers from said loading station to said entrance location, and subsequently through said opening in said housing and into said interior chamber using said conveyor belt, thereby automatically loading said specimen container into said detection apparatus.

13. The method of claim 12, wherein said interior chamber comprises an incubation chamber said incubation chamber comprising one or more heating elements to provide and/or maintain a climate-controlled interior chamber for promoting and/or enhancing microorganism growth therein.

14. The method of claim 12, wherein said method further comprises moving said specimen container among one or more work stations using said container locator device.

15. The method of claim 14, further comprising moving said specimen container to a pick-up station using said container locator device, and up said specimen container from said pick-up station using an automated transfer mechanism and subsequently transferring said specimen container from said pick-up station to a holding structure contained within said interior chamber.

16. The method of claim 15, wherein said detection apparatus further comprises a controller, and wherein said controller is operable to control one or more steps of said method.

* * * * *